(12) United States Patent
Brinkmann et al.

(10) Patent No.: US 8,361,747 B2
(45) Date of Patent: Jan. 29, 2013

(54) ANTIBODIES AGAINST HUMAN ANGIOPOIETIN 2

(75) Inventors: Ulrich Brinkmann, Weilheim (DE); Remko Albert Griep, Slemmestad (NO); Klaus Kaluza, Bad Heilbrunn (DE); Anita Kavlie, Oslo (NO); Christian Klein, Iffeldorf (DE); Joerg Thomas Regula, Munich (DE); Werner Scheuer, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/358,813

(22) Filed: Jan. 26, 2012

(65) Prior Publication Data

US 2012/0142091 A1 Jun. 7, 2012

Related U.S. Application Data

(62) Division of application No. 12/635,825, filed on Dec. 11, 2009, now Pat. No. 8,133,979.

(30) Foreign Application Priority Data

Dec. 16, 2008 (EP) .................... 08021835

(51) Int. Cl.
*C12P 21/06* (2006.01)
*C12N 15/87* (2006.01)
*C12N 1/20* (2006.01)
*C12N 15/74* (2006.01)
*C07H 21/04* (2006.01)

(52) U.S. Cl. ........ 435/69.1; 435/455; 435/325; 435/326; 435/252.3; 435/320.1; 536/23.53

(58) Field of Classification Search .................. None
See application file for complete search history.

(56) References Cited

U.S. PATENT DOCUMENTS

| 5,859,205 | A | 1/1999 | Adair et al. |
| 6,166,185 | A | 12/2000 | Davis et al. |
| 8,133,979 | B2 * | 3/2012 | Brinkmann et al. ....... 530/387.3 |
| 2003/0124129 | A1 | 7/2003 | Oliner et al. |
| 2006/0122370 | A1 | 6/2006 | Oliner et al. |
| 2010/0111967 | A1 | 5/2010 | Baehner et al. |

FOREIGN PATENT DOCUMENTS

| WO | 03/057134 | 3/2003 |
| WO | 03/030833 | 4/2003 |
| WO | 2006/045049 | 4/2006 |
| WO | 2006/068953 | 6/2006 |
| WO | 2007/033216 | 3/2007 |
| WO | 2007/068895 | 6/2007 |
| WO | 2010/040508 | 4/2010 |

OTHER PUBLICATIONS

Casset et al., Biochem. Biophys. Res. Commun. 307(1):198-205 (2003).
Paul, Fundamental Immunology, (3rd Edition):292-295 (1993).
Rudikoff et al., Proc. Natl. Acad. Sci. USA, 79(6):1979-1983 (Mar. 1982).
Thomas et al., EJC Supplements, 8(7):156-157 (Nov. 2010).
MacCallum et al., J. Mol. Biol., 262(5):732-745 (Oct. 1996).
Padlan, Mol. Immunol., 31(3):169-217 (Feb. 1994).
Klimka et al., British Journal of Cancer, 83:252-260 ( 2000).
Oliner et al., Cell Press, US 6(5):507-516 ( 2004).
Translation of Taiwanese Off Act in Corres Taiwan App 098142952 Jul. 2, 2012.

* cited by examiner

*Primary Examiner* — Maher Haddad
(74) *Attorney, Agent, or Firm* — George W. Johnston; Patricia S. Rocha-Tramaloni; Gene J. Yao

(57) ABSTRACT

The present invention relates to antibodies against human Angiopoietin 2 (anti-ANG-2 antibodies), methods for their production, pharmaceutical compositions containing said antibodies, and uses thereof.

4 Claims, 13 Drawing Sheets

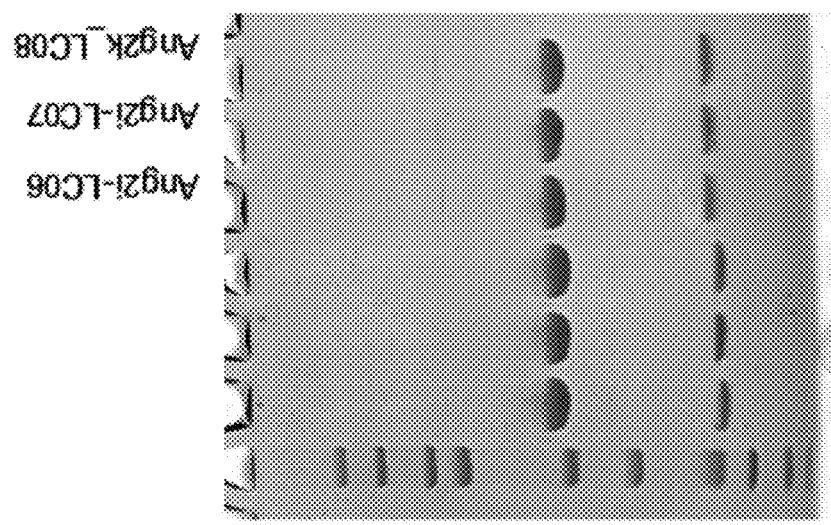
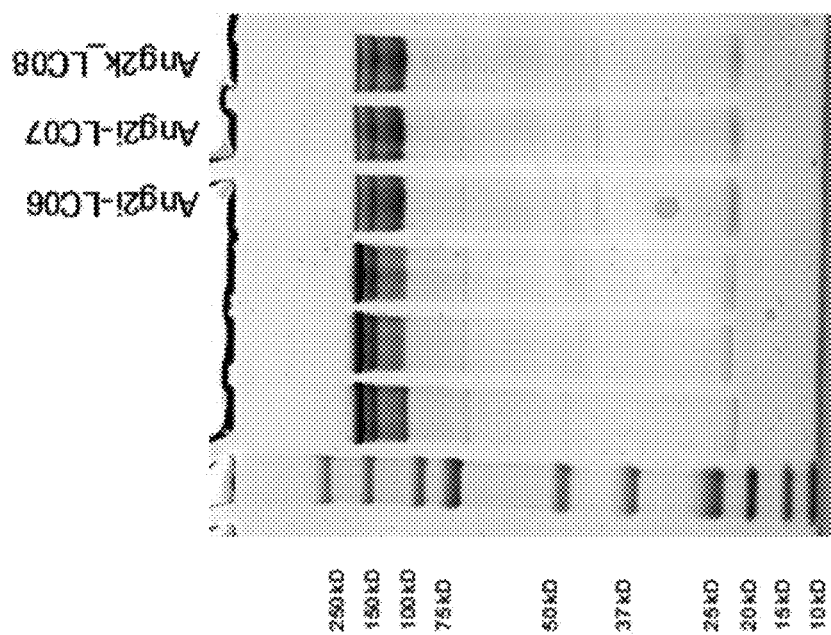

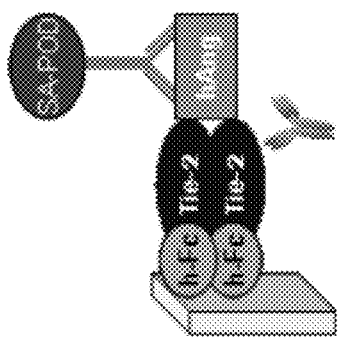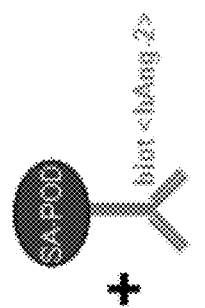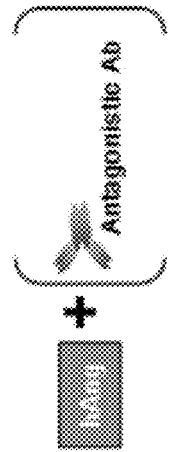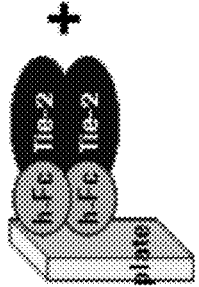
Fig. 3

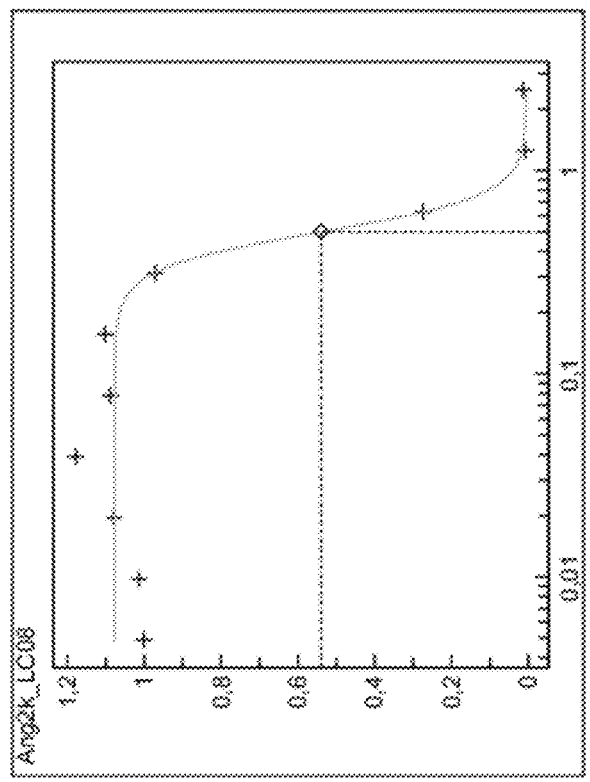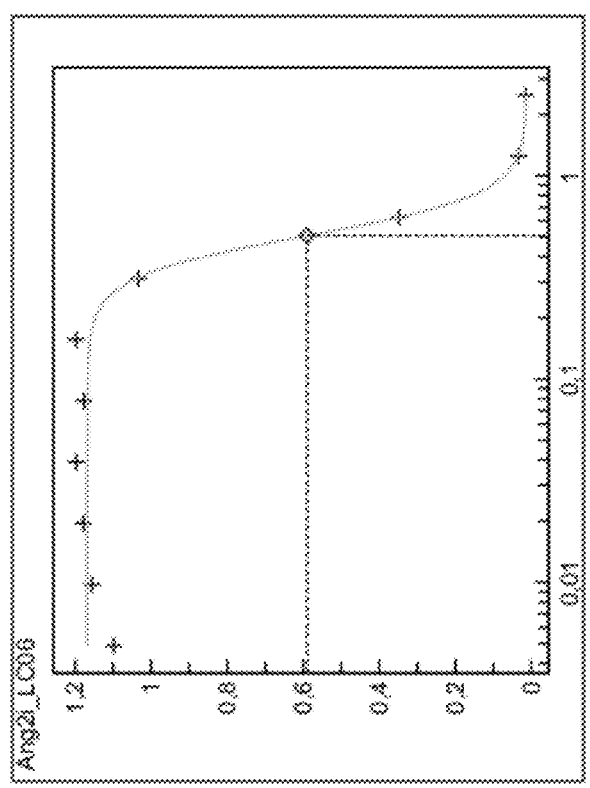
Fig. 4

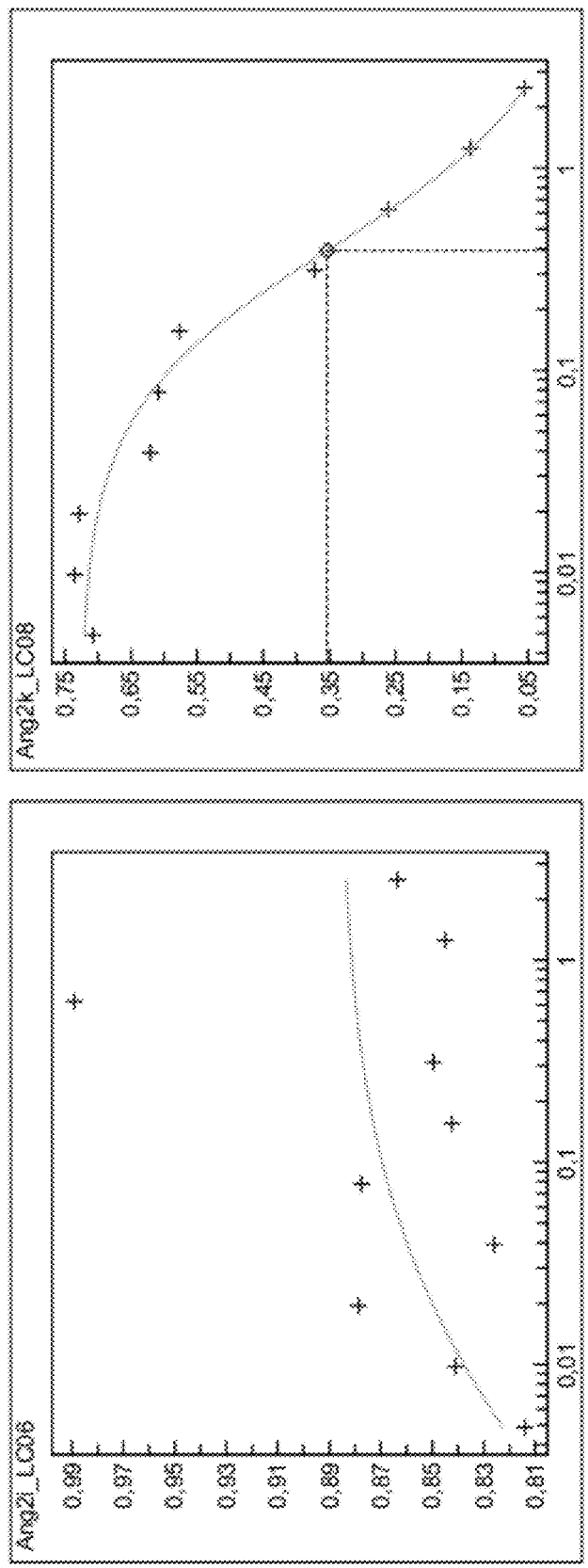

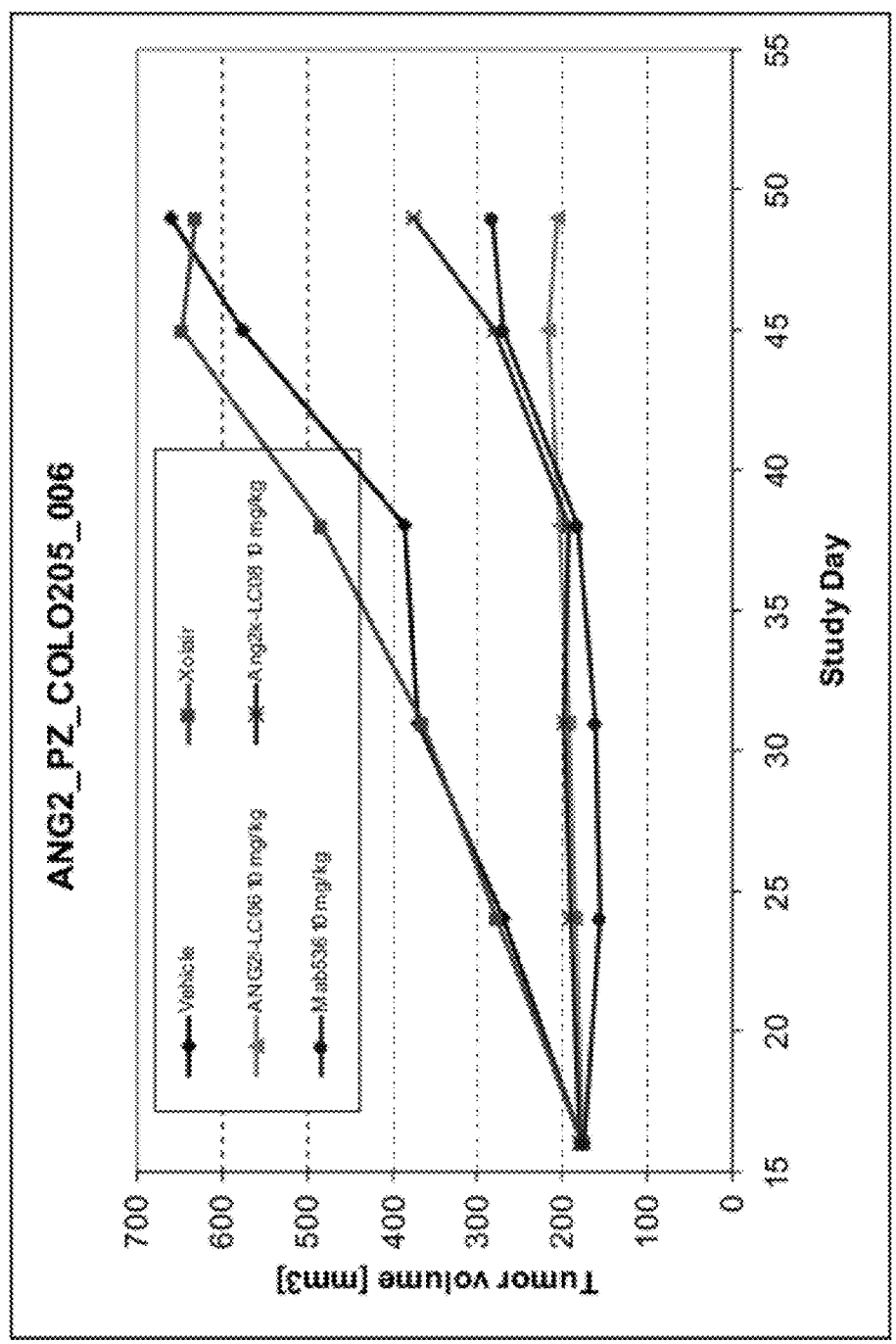

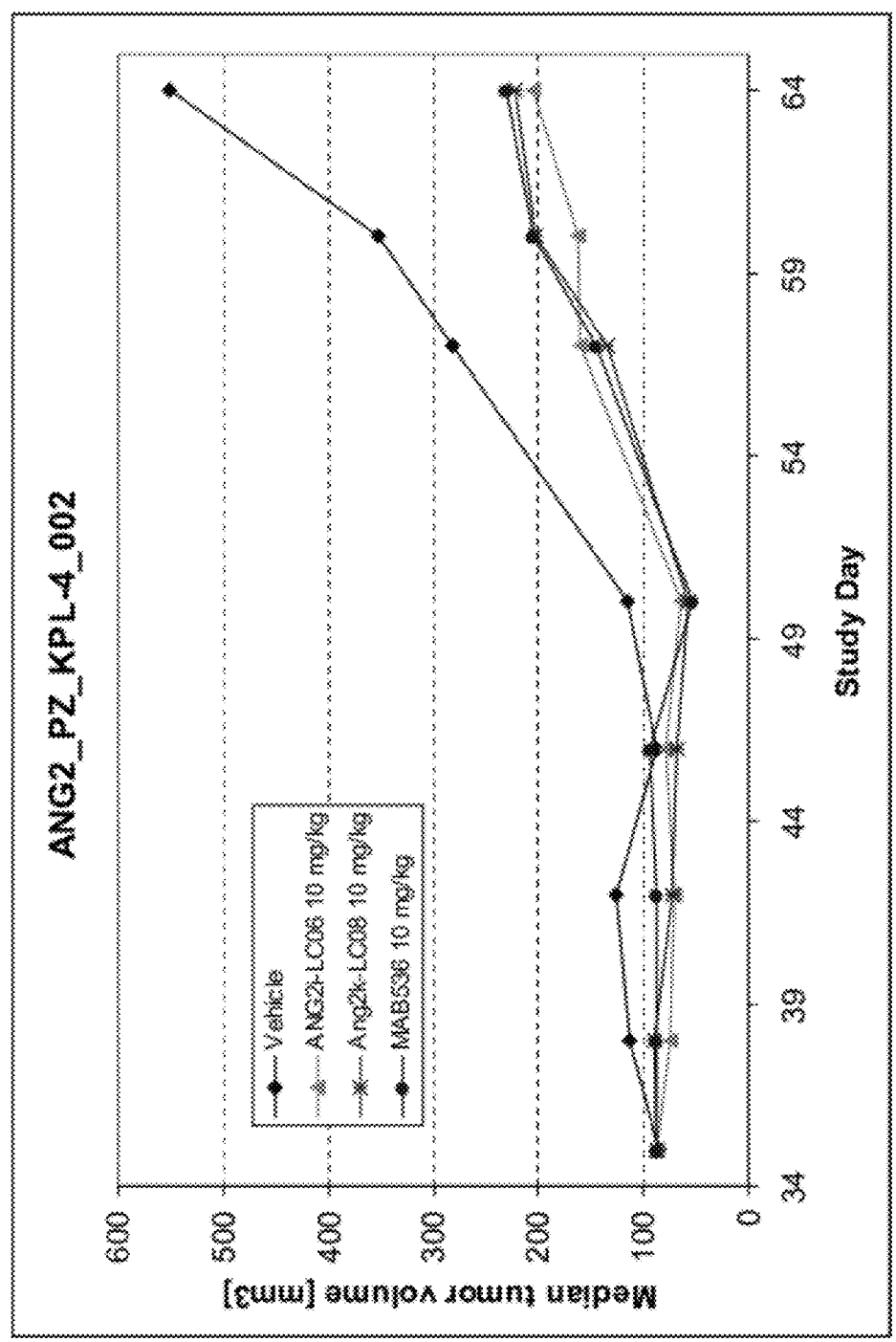

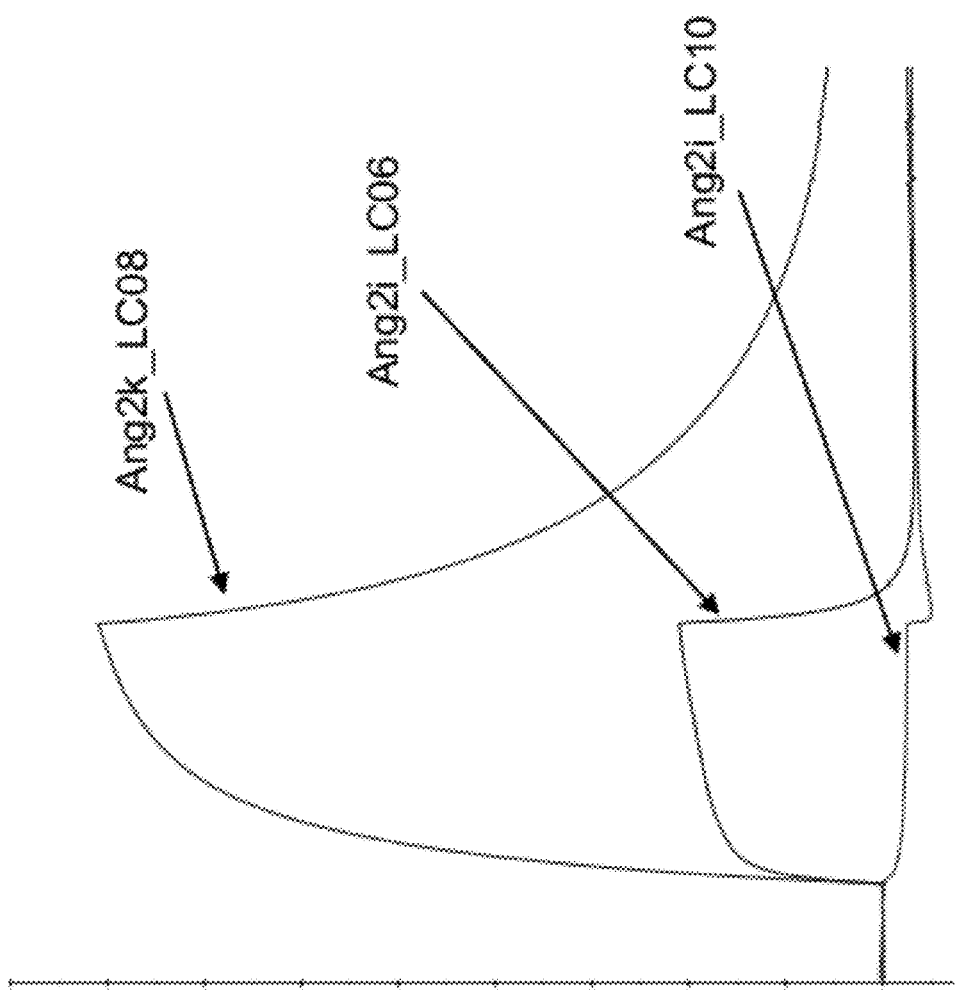

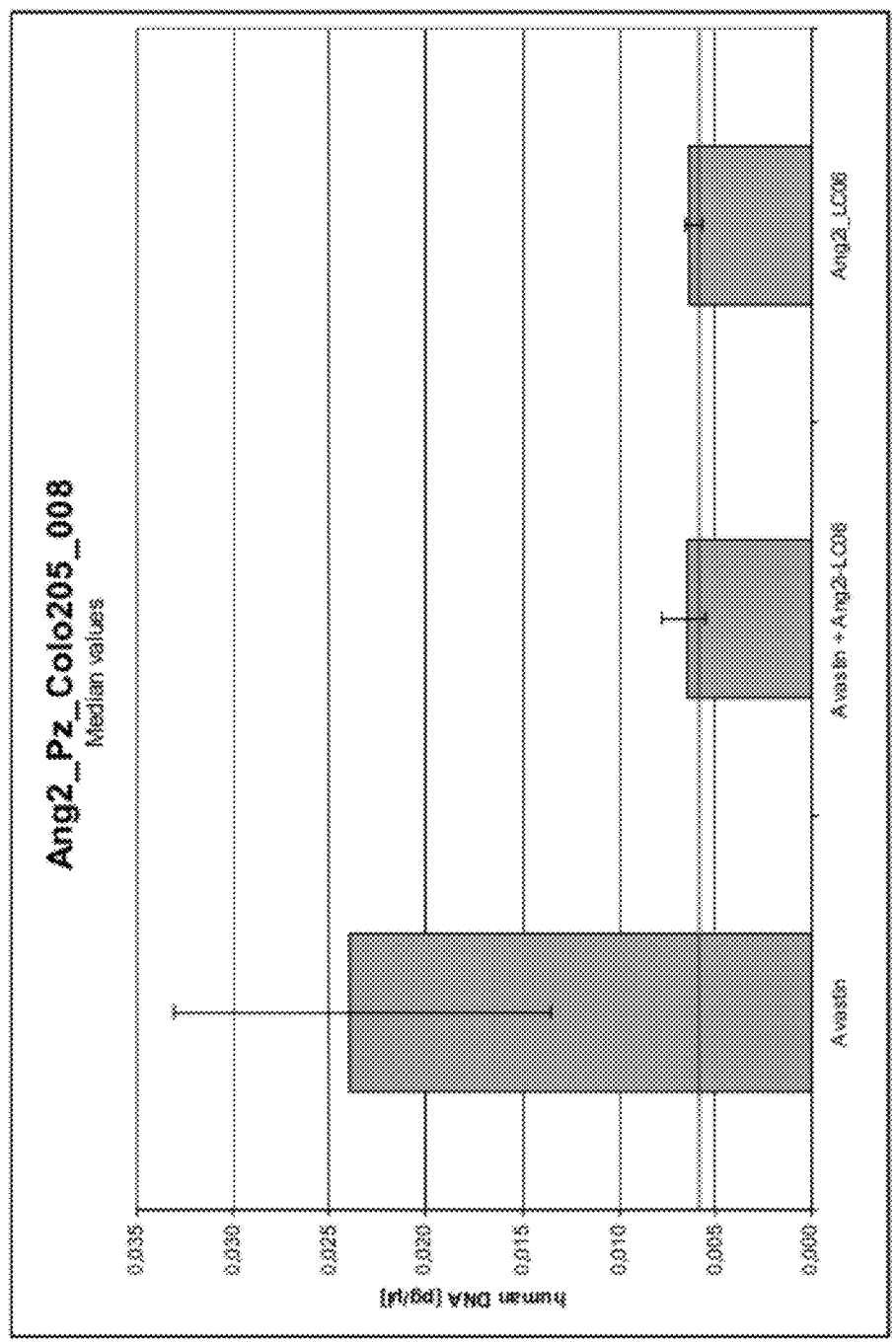

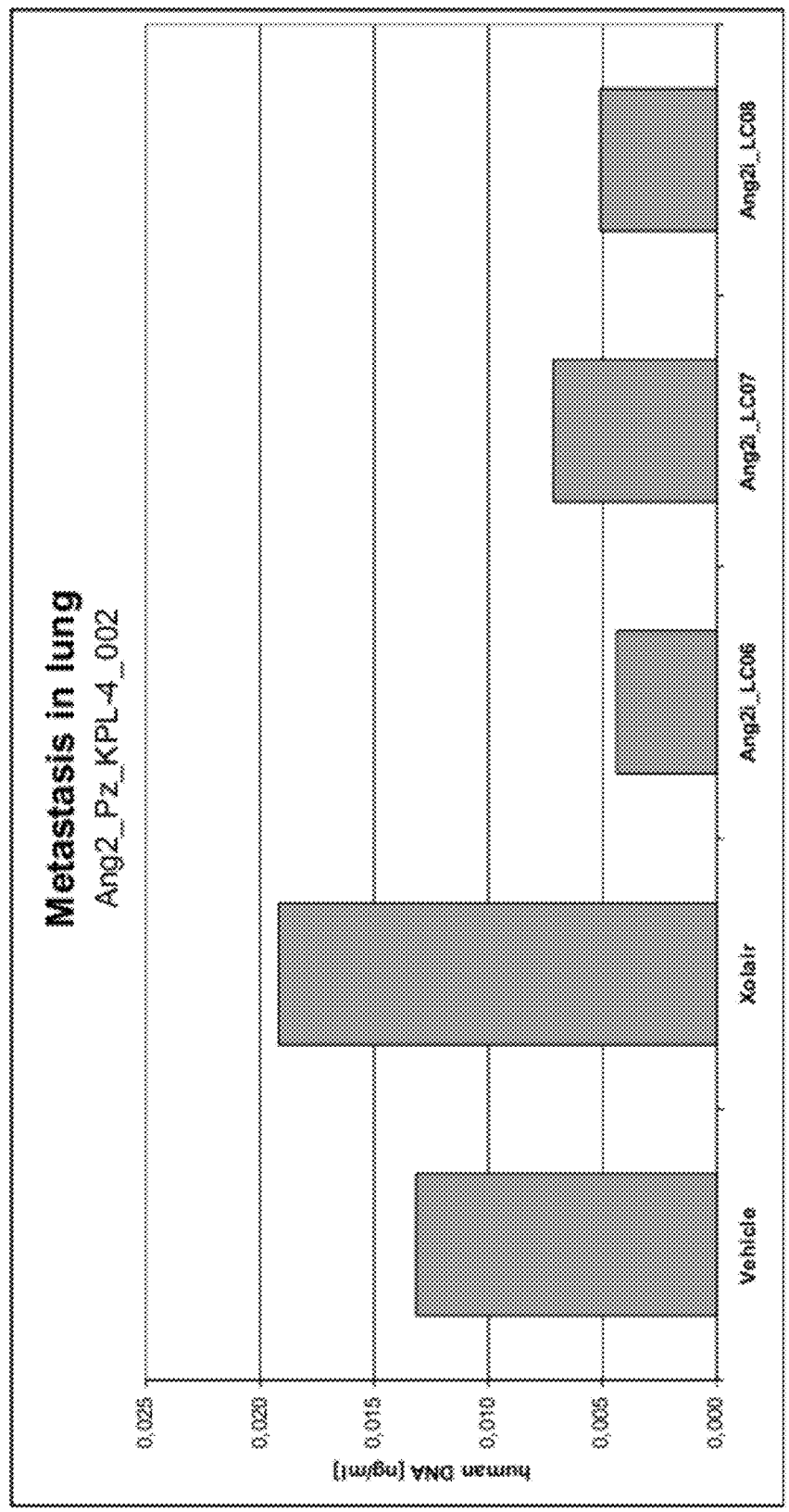

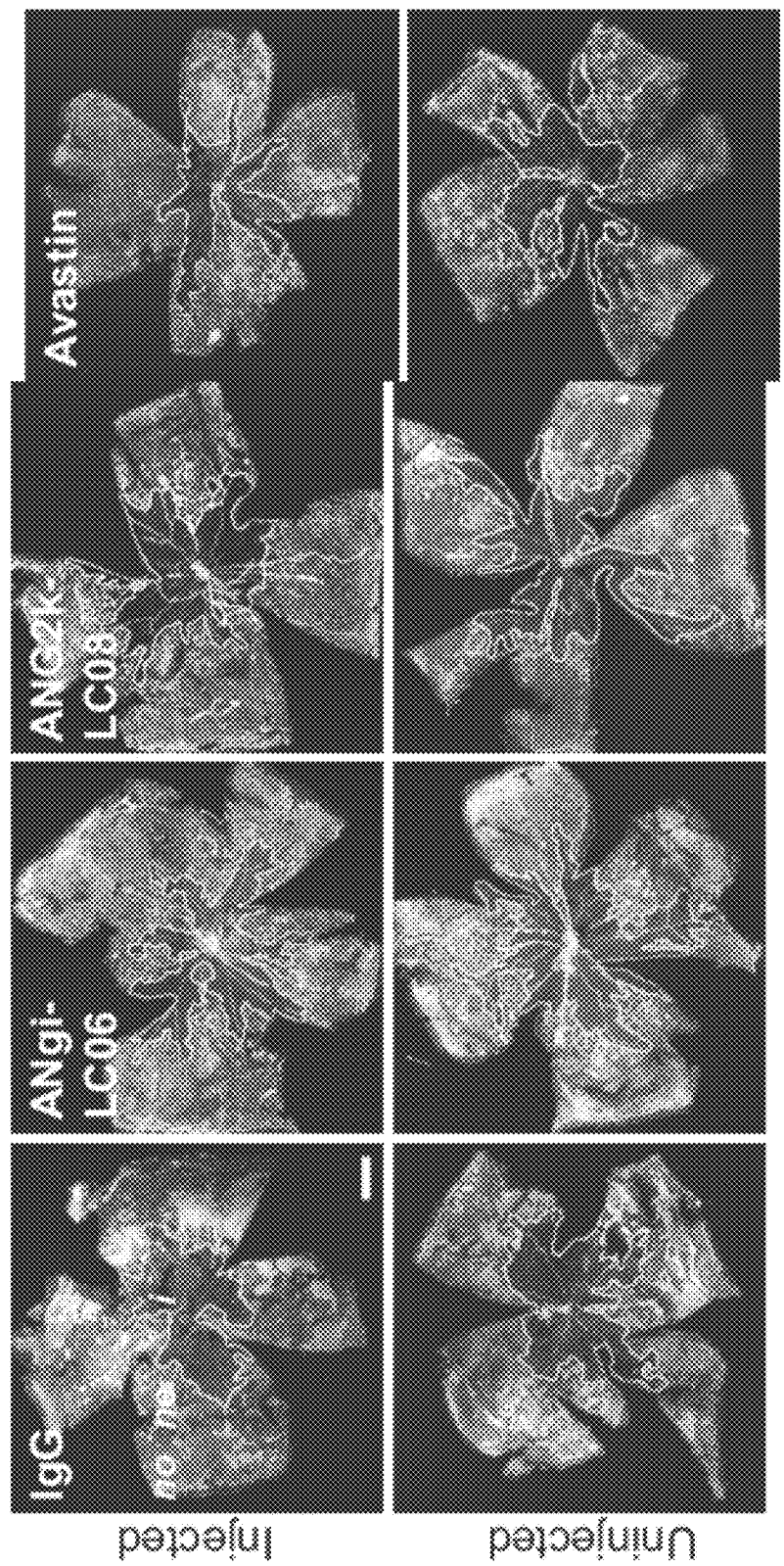

```
                        SEQUENCE LISTING

<160> NUMBER OF SEQ ID NOS: 63

<210> SEQ ID NO 1
<211> LENGTH: 20
<212> TYPE: PRT
<213> ORGANISM: Artificial
<220> FEATURE:
<223> OTHER INFORMATION: heavy chain CDR3, <ANG-2>Ang2i_LC06

<400> SEQUENCE: 1

Ser Pro Asn Pro Tyr Tyr Tyr Asp Ser Ser Gly Tyr Tyr Tyr Pro Gly
1               5                   10                  15

Ala Phe Asp Ile
            20

<210> SEQ ID NO 2
<211> LENGTH: 17
<212> TYPE: PRT
<213> ORGANISM: Artificial
<220> FEATURE:
<223> OTHER INFORMATION: heavy chain CDR2, <ANG-2>Ang2i_LC06

<400> SEQUENCE: 2

Trp Ile Asn Pro Asn Ser Gly Gly Thr Asn Tyr Ala Gln Lys Phe Gln
1               5                   10                  15

Gly

<210> SEQ ID NO 3
<211> LENGTH: 5
<212> TYPE: PRT
<213> ORGANISM: Artificial
<220> FEATURE:
<223> OTHER INFORMATION: heavy chain CDR1, <ANG-2>Ang2i_LC06

<400> SEQUENCE: 3

Gly Tyr Tyr Met His
1               5
```

```
<210> SEQ ID NO 4
<211> LENGTH: 11
<212> TYPE: PRT
<213> ORGANISM: Artificial
<220> FEATURE:
<223> OTHER INFORMATION: light chain CDR3, <ANG-2>Ang2i_LC06

<400> SEQUENCE: 4

Gln Val Trp Asp Ser Ser Ser Asp His Tyr Val
1               5                   10

<210> SEQ ID NO 5
<211> LENGTH: 7
<212> TYPE: PRT
<213> ORGANISM: Artificial
<220> FEATURE:
<223> OTHER INFORMATION: light chain CDR2, <ANG-2>Ang2i_LC06

<400> SEQUENCE: 5

Asp Asp Ser Asp Arg Pro Ser
1               5

<210> SEQ ID NO 6
<211> LENGTH: 11
<212> TYPE: PRT
<213> ORGANISM: Artificial
<220> FEATURE:
<223> OTHER INFORMATION: light chain CDR1, <ANG-2>Ang2i_LC06

<400> SEQUENCE: 6

Gly Gly Asn Asn Ile Gly Ser Lys Ser Val His
1               5                   10

<210> SEQ ID NO 7
<211> LENGTH: 129
<212> TYPE: PRT
<213> ORGANISM: Artificial
<220> FEATURE:
<223> OTHER INFORMATION: heavy chain variable domain, <ANG-2>Ang2i_LC06

<400> SEQUENCE: 7

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser

<210> SEQ ID NO 8
<211> LENGTH: 110
<212> TYPE: PRT
<213> ORGANISM: Artificial
```

-continued

```
<220> FEATURE:
<223> OTHER INFORMATION: light chain variable domain, <ANG-2>Ang2i_LC06

<400> SEQUENCE: 8

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Gln
            100                 105                 110

<210> SEQ ID NO 9
<211> LENGTH: 20
<212> TYPE: PRT
<213> ORGANISM: Artificial
<220> FEATURE:
<223> OTHER INFORMATION: heavy chain CDR3, <ANG-2>Ang2i_LC07

<400> SEQUENCE: 9

Ser Pro Asn Pro Tyr Tyr Tyr Asp Ser Ser Gly Tyr Tyr Tyr Pro Gly
1               5                   10                  15

Ala Phe Asp Ile
            20

<210> SEQ ID NO 10
<211> LENGTH: 17
<212> TYPE: PRT
<213> ORGANISM: Artificial
<220> FEATURE:
<223> OTHER INFORMATION: heavy chain CDR2, <ANG-2>Ang2i_LC07

<400> SEQUENCE: 10

Trp Ile Asn Pro Asn Ser Gly Gly Thr Asn Tyr Ala Gln Lys Phe Gln
1               5                   10                  15

Gly

<210> SEQ ID NO 11
<211> LENGTH: 5
<212> TYPE: PRT
<213> ORGANISM: Artificial
<220> FEATURE:
<223> OTHER INFORMATION: heavy chain CDR1, <ANG-2>Ang2i_LC07

<400> SEQUENCE: 11

Gly Tyr Tyr Met His
1               5

<210> SEQ ID NO 12
<211> LENGTH: 11
<212> TYPE: PRT
<213> ORGANISM: Artificial
<220> FEATURE:
<223> OTHER INFORMATION: light chain CDR3, <ANG-2>Ang2i_LC07

<400> SEQUENCE: 12
```

```
Gln Val Trp Asp Ser Asp Ser Asp Gln Gly Val
1               5                   10

<210> SEQ ID NO 13
<211> LENGTH: 7
<212> TYPE: PRT
<213> ORGANISM: Artificial
<220> FEATURE:
<223> OTHER INFORMATION: light chain CDR2, <ANG-2>Ang2i_LC07

<400> SEQUENCE: 13

Asp Asp Ser Glu Arg Pro Ser
1               5

<210> SEQ ID NO 14
<211> LENGTH: 11
<212> TYPE: PRT
<213> ORGANISM: Artificial
<220> FEATURE:
<223> OTHER INFORMATION: light chain CDR1, <ANG-2>Ang2i_LC07

<400> SEQUENCE: 14

Gly Gly Asn Phe Ile Gly Gly Lys Ser Val His
1               5                   10

<210> SEQ ID NO 15
<211> LENGTH: 129
<212> TYPE: PRT
<213> ORGANISM: Artificial
<220> FEATURE:
<223> OTHER INFORMATION: heavy chain variable domain, <ANG-2>Ang2i_LC07

<400> SEQUENCE: 15

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser

<210> SEQ ID NO 16
<211> LENGTH: 110
<212> TYPE: PRT
<213> ORGANISM: Artificial
<220> FEATURE:
<223> OTHER INFORMATION: light chain variable domain, <ANG-2>Ang2i_LC07

<400> SEQUENCE: 16

Gln Pro Val Leu Thr Gln Ser Pro Ser Val Ser Val Ala Pro Gly Glu
1               5                   10                  15

Thr Ala Arg Val Ala Cys Gly Gly Asn Phe Ile Gly Gly Lys Ser Val
                20                  25                  30
```

His Trp Tyr Gln Gln Lys Pro Gly Gln Ala Pro Val Leu Val Ile Tyr
            35                  40                  45

Asp Asp Ser Glu Arg Pro Ser Gly Ile Pro Glu Arg Ile Ser Gly Ser
 50                  55                  60

Asn Ser Gly Asn Thr Ala Thr Leu Ile Ile Thr Arg Ala Glu Ala Gly
 65                  70                  75                  80

Asp Glu Ala Asp Tyr His Cys Gln Val Trp Asp Ser Asp Ser Asp Gln
                 85                  90                  95

Gly Val Phe Gly Thr Gly Thr Lys Leu Thr Val Leu Gly Gln
            100                 105                 110

<210> SEQ ID NO 17
<211> LENGTH: 15
<212> TYPE: PRT
<213> ORGANISM: Artificial
<220> FEATURE:
<223> OTHER INFORMATION: heavy chain CDR3, <ANG-2>Ang2k_LC08

<400> SEQUENCE: 17

Pro Thr Leu Asp Ile Tyr Met Gly Tyr Tyr Tyr Gly Met Asp Val
1               5                   10                  15

<210> SEQ ID NO 18
<211> LENGTH: 17
<212> TYPE: PRT
<213> ORGANISM: Artificial
<220> FEATURE:
<223> OTHER INFORMATION: heavy chain CDR2, <ANG-2>Ang2k_LC08

<400> SEQUENCE: 18

Val Ile Ser Tyr Asp Gly Ser Asn Lys Tyr Tyr Ala Asp Ser Val Lys
1               5                   10                  15

Gly

<210> SEQ ID NO 19
<211> LENGTH: 5
<212> TYPE: PRT
<213> ORGANISM: Artificial
<220> FEATURE:
<223> OTHER INFORMATION: heavy chain CDR1, <ANG-2>Ang2k_LC08

<400> SEQUENCE: 19

Ser Tyr Gly Met His
1               5

<210> SEQ ID NO 20
<211> LENGTH: 11
<212> TYPE: PRT
<213> ORGANISM: Artificial
<220> FEATURE:
<223> OTHER INFORMATION: light chain CDR3, <ANG-2>Ang2k_LC08

<400> SEQUENCE: 20

Ala Ala Trp Asp Asp Ser Leu Asn Gly Pro Val
1               5                   10

<210> SEQ ID NO 21
<211> LENGTH: 7
<212> TYPE: PRT
<213> ORGANISM: Artificial
<220> FEATURE:
<223> OTHER INFORMATION: light chain CDR2, <ANG-2>Ang2k_LC08

<400> SEQUENCE: 21

Asn Asn Asp Gln Arg Pro Ser
1               5

<210> SEQ ID NO 22
<211> LENGTH: 13
<212> TYPE: PRT
<213> ORGANISM: Artificial
<220> FEATURE:
<223> OTHER INFORMATION: light chain CDR1, <ANG-2>Ang2k_LC08

<400> SEQUENCE: 22

Ser Gly Phe Ala Ser Asn Ile Gly Ser Asn Ser Val Asn
1               5                   10

<210> SEQ ID NO 23
<211> LENGTH: 124
<212> TYPE: PRT
<213> ORGANISM: Artificial
<220> FEATURE:
<223> OTHER INFORMATION: heavy chain variable domain, <ANG-2> Ang2k_LC08

<400> SEQUENCE: 23

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Leu Asp Ile Tyr Met Gly Tyr Tyr Gly Met Asp
            100                 105                 110

Val Trp Gly Gln Gly Thr Thr Val Thr Val Ser Ser
        115                 120

<210> SEQ ID NO 24
<211> LENGTH: 112
<212> TYPE: PRT
<213> ORGANISM: Artificial
<220> FEATURE:
<223> OTHER INFORMATION: light chain variable domain, <ANG-2> Ang2k_LC08

<400> SEQUENCE: 24

Gln Pro Val Leu Thr Gln Pro Pro Ser Ala Ser Gly Ala Pro Gly Gln
1               5                   10                  15

Arg Val Thr Ile Ser Cys Ser Gly Phe Ala Ser Asn Ile Gly Ser Asn
            20                  25                  30

Ser Val Asn Trp Tyr Gln Gln Val Pro Gly Thr Ala Pro Lys Leu Leu
        35                  40                  45

Ile Tyr Asn Asn Asp Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

```
<210> SEQ ID NO 25
<211> LENGTH: 7
<212> TYPE: PRT
<213> ORGANISM: Artificial
<220> FEATURE:
<223> OTHER INFORMATION: heavy chain CDR3, <ANG-2> Ang2s_LC09

<400> SEQUENCE: 25

Asp Leu Gly Tyr Asp Tyr Val
1               5

<210> SEQ ID NO 26
<211> LENGTH: 19
<212> TYPE: PRT
<213> ORGANISM: Artificial
<220> FEATURE:
<223> OTHER INFORMATION: heavy chain CDR2, <ANG-2> Ang2s_LC09

<400> SEQUENCE: 26

Arg Ile Lys Ser Lys Thr Asp Gly Gly Thr Thr Asp Tyr Ala Ala Pro
1               5                   10                  15

Val Lys Gly

<210> SEQ ID NO 27
<211> LENGTH: 5
<212> TYPE: PRT
<213> ORGANISM: Artificial
<220> FEATURE:
<223> OTHER INFORMATION: heavy chain CDR1, <ANG-2> Ang2s_LC09

<400> SEQUENCE: 27

Asn Ala Trp Met Ser
1               5

<210> SEQ ID NO 28
<211> LENGTH: 7
<212> TYPE: PRT
<213> ORGANISM: Artificial
<220> FEATURE:
<223> OTHER INFORMATION: light chain CDR3, <ANG-2> Ang2s_LC09

<400> SEQUENCE: 28

Met Gln Ala Leu Gln Ile Pro
1               5

<210> SEQ ID NO 29
<211> LENGTH: 7
<212> TYPE: PRT
<213> ORGANISM: Artificial
<220> FEATURE:
<223> OTHER INFORMATION: light chain CDR2, <ANG-2> Ang2s_LC09

<400> SEQUENCE: 29

Leu Gly Ser Asn Arg Ala Ser
1               5

<210> SEQ ID NO 30
<211> LENGTH: 16
<212> TYPE: PRT
<213> ORGANISM: Artificial
<220> FEATURE:
<223> OTHER INFORMATION: light chain CDR1, <ANG-2> Ang2s_LC09

<400> SEQUENCE: 30

Arg Ser Ser Gln Ser Leu Leu His Ser Asn Gly Tyr Asn Tyr Leu Asp
1               5                   10                  15
```

<210> SEQ ID NO 31
<211> LENGTH: 119
<212> TYPE: PRT
<213> ORGANISM: Artificial
<220> FEATURE:
<223> OTHER INFORMATION: heavy chain variable domain, <ANG-2> Ang2s_LC09

<400> SEQUENCE: 31

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Leu Gly Tyr Asp Tyr Val Trp Gly Ser Pro Gly
            100                 105                 110

Thr Leu Val Thr Val Ser Ser
        115
```

<210> SEQ ID NO 32
<211> LENGTH: 109
<212> TYPE: PRT
<213> ORGANISM: Artificial
<220> FEATURE:
<223> OTHER INFORMATION: light chain variable domain, <ANG-2> Ang2s_LC09

<400> SEQUENCE: 32

```
Gln Ser Pro Leu Ser Leu Pro Val Thr Pro Gly Glu Pro Ala Ser Ile
1               5                   10                  15

Ser Cys Arg Ser Ser Gln Ser Leu Leu His Ser Asn Gly Tyr Asn Tyr
            20                  25                  30

Leu Asp Trp Tyr Leu Gln Lys Pro Gly Gln Ser Pro Gln Leu Leu Ile
        35                  40                  45

Tyr Leu Gly Ser Asn Arg Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Met Gln Ala Leu Gln Ile Pro Phe
                85                  90                  95

Thr Phe Gly Pro Gly Thr Lys Val Thr Val Leu Arg Thr
            100                 105
```

<210> SEQ ID NO 33
<211> LENGTH: 20
<212> TYPE: PRT
<213> ORGANISM: Artificial
<220> FEATURE:
<223> OTHER INFORMATION: heavy chain CDR3, <ANG-2> Ang2i_LC10

<400> SEQUENCE: 33

```
Ser Pro Asn Pro Tyr Tyr Tyr Asp Ser Ser Gly Tyr Tyr Tyr Pro Gly
1               5                   10                  15

Ala Phe Asp Ile
```

<210> SEQ ID NO 34
<211> LENGTH: 17
<212> TYPE: PRT
<213> ORGANISM: Artificial
<220> FEATURE:
<223> OTHER INFORMATION: heavy chain CDR2, <ANG-2> Ang2i_LC10

<400> SEQUENCE: 34

Trp Ile Asn Pro Asn Ser Gly Gly Thr Asn Tyr Ala Gln Lys Phe Gln
1               5                   10                  15
Gly

<210> SEQ ID NO 35
<211> LENGTH: 5
<212> TYPE: PRT
<213> ORGANISM: Artificial
<220> FEATURE:
<223> OTHER INFORMATION: heavy chain CDR1, <ANG-2> Ang2i_LC10

<400> SEQUENCE: 35

Gly Tyr Tyr Met His
1               5

<210> SEQ ID NO 36
<211> LENGTH: 11
<212> TYPE: PRT
<213> ORGANISM: Artificial
<220> FEATURE:
<223> OTHER INFORMATION: light chain CDR3, <ANG-2> Ang2i_LC10

<400> SEQUENCE: 36

Gln Val Trp Asp Ser Ser Ser Asp His Trp Val
1               5                   10

<210> SEQ ID NO 37
<211> LENGTH: 7
<212> TYPE: PRT
<213> ORGANISM: Artificial
<220> FEATURE:
<223> OTHER INFORMATION: light chain CDR2, <ANG-2> Ang2i_LC10

<400> SEQUENCE: 37

Asp Asp Ser Asp Arg Pro Ser
1               5

<210> SEQ ID NO 38
<211> LENGTH: 11
<212> TYPE: PRT
<213> ORGANISM: Artificial
<220> FEATURE:
<223> OTHER INFORMATION: light chain CDR1, <ANG-2> Ang2i_LC10

<400> SEQUENCE: 38

Gly Gly Asn Asn Ile Gly Ser Lys Ser Val His
1               5                   10

<210> SEQ ID NO 39
<211> LENGTH: 129
<212> TYPE: PRT
<213> ORGANISM: Artificial
<220> FEATURE:
<223> OTHER INFORMATION: heavy chain variable domain, <ANG-2> Ang2i_LC10

<400> SEQUENCE: 39

Gln Val Gln Leu Val Glu Ser Gly Ala Glu Val Lys Lys Pro Gly Ala

```
                1               5                  10                 15
Ser Val Lys Val Ser Cys Lys Ala Ser Gly Tyr Thr Phe Thr Gly Tyr
                    20                 25                 30

Tyr Met His Trp Val Arg Gln Ala Pro Gly Gln Gly Leu Glu Trp Met
            35                 40                 45

Gly Trp Ile Asn Pro Asn Ser Gly Gly Thr Asn Tyr Ala Gln Lys Phe
    50                 55                 60

Gln Gly Arg Val Thr Met Thr Arg Asp Thr Ser Ile Ser Thr Ala Tyr
65                 70                 75                 80

Met Glu Leu Ser Arg Leu Arg Ser Asp Asp Thr Ala Val Tyr Tyr Cys
                85                 90                 95

Ala Arg Ser Pro Asn Pro Tyr Tyr Tyr Asp Ser Ser Gly Tyr Tyr Tyr
                100                105                110

Pro Gly Ala Phe Asp Ile Trp Gly Gln Gly Thr Met Val Thr Val Ser
                115                120                125

Ser

<210> SEQ ID NO 40
<211> LENGTH: 105
<212> TYPE: PRT
<213> ORGANISM: Artificial
<220> FEATURE:
<223> OTHER INFORMATION: light chain variable domain, <ANG-2> Ang2i_LC10

<400> SEQUENCE: 40

Gln Pro Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
                20                  25                  30

Lys Pro Gly Gln Ala Pro Val Leu Val Val Tyr Asp Asp Ser Asp Arg
            35                  40                  45

Pro Ser Gly Ile Pro Glu Arg Phe Ser Gly Ser Asn Ser Gly Asn Thr
        50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Asp His Trp Val Phe Gly Gly
                85                  90                  95

Gly Thr Lys Leu Thr Val Leu Gly Gln
                100                 105

<210> SEQ ID NO 41
<211> LENGTH: 15
<212> TYPE: PRT
<213> ORGANISM: Artificial
<220> FEATURE:
<223> OTHER INFORMATION: heavy chain CDR3, <ANG-2> Ang2k_LC11

<400> SEQUENCE: 41

Pro Thr Leu Asp Ile Tyr Met Gly Tyr Tyr Tyr Gly Met Asp Val
1               5                   10                  15

<210> SEQ ID NO 42
<211> LENGTH: 17
<212> TYPE: PRT
<213> ORGANISM: Artificial
<220> FEATURE:
<223> OTHER INFORMATION: heavy chain CDR2, <ANG-2> Ang2k_LC11

<400> SEQUENCE: 42

Val Ile Ser Tyr Asp Gly Ser Asn Lys Tyr Tyr Ala Asp Ser Val Lys
```

1               5                   10                  15
Gly

<210> SEQ ID NO 43
<211> LENGTH: 5
<212> TYPE: PRT
<213> ORGANISM: Artificial
<220> FEATURE:
<223> OTHER INFORMATION: heavy chain CDR1, <ANG-2> Ang2k_LC11

<400> SEQUENCE: 43

Ser Tyr Gly Met His
1               5

<210> SEQ ID NO 44
<211> LENGTH: 12
<212> TYPE: PRT
<213> ORGANISM: Artificial
<220> FEATURE:
<223> OTHER INFORMATION: light chain CDR3, <ANG-2> Ang2k_LC11

<400> SEQUENCE: 44

Gln Val Trp Asp Ser Ser Ser Asp His Pro Gly Val
1               5                   10

<210> SEQ ID NO 45
<211> LENGTH: 7
<212> TYPE: PRT
<213> ORGANISM: Artificial
<220> FEATURE:
<223> OTHER INFORMATION: light chain CDR2, <ANG-2> Ang2k_LC11

<400> SEQUENCE: 45

Asp Asp Ser Asp Arg Pro Ser
1               5

<210> SEQ ID NO 46
<211> LENGTH: 11
<212> TYPE: PRT
<213> ORGANISM: Artificial
<220> FEATURE:
<223> OTHER INFORMATION: light chain CDR1, <ANG-2> Ang2k_LC11

<400> SEQUENCE: 46

Gly Gly Asn Asn Ile Gly Ser Lys Ser Val His
1               5                   10

<210> SEQ ID NO 47
<211> LENGTH: 124
<212> TYPE: PRT
<213> ORGANISM: Artificial
<220> FEATURE:
<223> OTHER INFORMATION: heavy chain variable domain, <ANG-2> Ang2k_LC11

<400> SEQUENCE: 47

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Pro Thr Leu Asp Ile Tyr Met Gly Tyr Tyr Gly Met Asp
            100                 105                 110

Val Trp Gly Gln Gly Thr Thr Val Thr Val Ser Ser
        115                 120
```

<210> SEQ ID NO 48
<211> LENGTH: 106
<212> TYPE: PRT
<213> ORGANISM: Artificial
<220> FEATURE:
<223> OTHER INFORMATION: light chain variable domain, <ANG-2> Ang2k_LC11
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 48

```
Gln Pro Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
                20                  25                  30

Lys Pro Gly Gln Ala Pro Val Leu Val Val Tyr Asp Asp Ser Asp Arg
            35                  40                  45

Pro Ser Gly Ile Pro Glu Arg Phe Ser Gly Ser Asn Ser Gly Asn Thr
    50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Ser Asp His Pro Gly Val Phe Gly
                85                  90                  95

Gly Xaa Thr Lys Leu Xaa Val Leu Gly Gln
            100                 105
```

<210> SEQ ID NO 49
<211> LENGTH: 7
<212> TYPE: PRT
<213> ORGANISM: Artificial
<220> FEATURE:
<223> OTHER INFORMATION: heavy chain CDR3, <ANG-2> Ang2s_R3_LC03

<400> SEQUENCE: 49

```
Asp Leu Gly Tyr Asp Tyr Val
1               5
```

<210> SEQ ID NO 50
<211> LENGTH: 19
<212> TYPE: PRT
<213> ORGANISM: Artificial
<220> FEATURE:
<223> OTHER INFORMATION: heavy chain CDR2, <ANG-2> Ang2s_R3_LC03

<400> SEQUENCE: 50

```
Arg Ile Lys Ser Lys Thr Asp Gly Gly Thr Thr Asp Tyr Ala Ala Pro
1               5                   10                  15

Val Lys Gly
```

<210> SEQ ID NO 51
<211> LENGTH: 5

```
<212> TYPE: PRT
<213> ORGANISM: Artificial
<220> FEATURE:
<223> OTHER INFORMATION: heavy chain CDR1, <ANG-2> Ang2s_R3_LC03

<400> SEQUENCE: 51

Asn Ala Trp Met Ser
1               5

<210> SEQ ID NO 52
<211> LENGTH: 10
<212> TYPE: PRT
<213> ORGANISM: Artificial
<220> FEATURE:
<223> OTHER INFORMATION: light chain CDR3, <ANG-2> Ang2s_R3_LC03

<400> SEQUENCE: 52

Gln Gln Tyr Asp Asn Leu Pro Met Tyr Thr
1               5                   10

<210> SEQ ID NO 53
<211> LENGTH: 7
<212> TYPE: PRT
<213> ORGANISM: Artificial
<220> FEATURE:
<223> OTHER INFORMATION: light chain CDR2, <ANG-2> Ang2s_R3_LC03

<400> SEQUENCE: 53

His Ala Ser Asn Leu Glu Thr
1               5

<210> SEQ ID NO 54
<211> LENGTH: 11
<212> TYPE: PRT
<213> ORGANISM: Artificial
<220> FEATURE:
<223> OTHER INFORMATION: light chain CDR1, <ANG-2> Ang2s_R3_LC03

<400> SEQUENCE: 54

Gln Ala Ser Gln Asp Ile Ser Asn Arg Leu Asn
1               5                   10

<210> SEQ ID NO 55
<211> LENGTH: 118
<212> TYPE: PRT
<213> ORGANISM: Artificial
<220> FEATURE:
<223> OTHER INFORMATION: heavy chain variable domain, <ANG-2>
      Ang2s_R3_LC03

<400> SEQUENCE: 55

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Leu Gly Tyr Asp Tyr Val Trp Gly Gln Gly Thr
            100                 105                 110
```

-continued

```
Leu Val Thr Val Ser Ser
        115

<210> SEQ ID NO 56
<211> LENGTH: 110
<212> TYPE: PRT
<213> ORGANISM: Artificial
<220> FEATURE:
<223> OTHER INFORMATION: light chain variable domain,<ANG-2>
      Ang2s_R3_LC03

<400> SEQUENCE: 56

Asp Ile Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Arg
            20                  25                  30

Leu Asn Trp Tyr Gln Gln Lys Pro Gly Lys Ala Pro Lys Leu Leu Ile
        35                  40                  45

Tyr His Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Met
                85                  90                  95

Tyr Thr Phe Gly Gln Gly Thr Lys Leu Glu Ile Lys Arg Thr
            100                 105                 110

<210> SEQ ID NO 57
<211> LENGTH: 330
<212> TYPE: PRT
<213> ORGANISM: Homo sapiens

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 58
<211> LENGTH: 327
<212> TYPE: PRT
<213> ORGANISM: Homo sapiens

<400> SEQUENCE: 58

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
```

-continued

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 59
<211> LENGTH: 107
<212> TYPE: PRT
<213> ORGANISM: Homo sapiens

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 60
<211> LENGTH: 104
<212> TYPE: PRT
<213> ORGANISM: Homo sapiens

<400> SEQUENCE: 60

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 61
<211> LENGTH: 1124
<212> TYPE: PRT

<213> ORGANISM: Homo sapiens

<400> SEQUENCE: 61

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
```

-continued

```
                405                 410                 415
Pro Asp Ser Gly Val Trp Val Cys Ser Val Asn Thr Val Ala Gly Met
            420                 425                 430
Val Glu Lys Pro Phe Asn Ile Ser Val Lys Val Leu Pro Lys Pro Leu
        435                 440                 445
Asn Ala Pro Asn Val Ile Asp Thr Gly His Asn Phe Ala Val Ile Asn
    450                 455                 460
Ile Ser Ser Glu Pro Tyr Phe Gly Asp Gly Pro Ile Lys Ser Lys Lys
465                 470                 475                 480
Leu Leu Tyr Lys Pro Val Asn His Tyr Glu Ala Trp Gln His Ile Gln
                485                 490                 495
Val Thr Asn Glu Ile Val Thr Leu Asn Tyr Leu Glu Pro Arg Thr Glu
            500                 505                 510
Tyr Glu Leu Cys Val Gln Leu Val Arg Arg Gly Glu Gly Gly Glu Gly
        515                 520                 525
His Pro Gly Pro Val Arg Arg Phe Thr Thr Ala Ser Ile Gly Leu Pro
    530                 535                 540
Pro Pro Arg Gly Leu Asn Leu Leu Pro Lys Ser Gln Thr Thr Leu Asn
545                 550                 555                 560
Leu Thr Trp Gln Pro Ile Phe Pro Ser Ser Glu Asp Asp Phe Tyr Val
                565                 570                 575
Glu Val Glu Arg Arg Ser Val Gln Lys Ser Asp Gln Asn Ile Lys
            580                 585                 590
Val Pro Gly Asn Leu Thr Ser Val Leu Leu Asn Asn Leu His Pro Arg
        595                 600                 605
Glu Gln Tyr Val Val Arg Ala Arg Val Asn Thr Lys Ala Gln Gly Glu
    610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                645                 650                 655
Ile Ser Trp Thr Ile Leu Asp Gly Tyr Ser Ile Ser Ser Ile Thr Ile
            660                 665                 670
Arg Tyr Lys Val Gln Gly Lys Asn Glu Asp Gln His Val Asp Val Lys
        675                 680                 685
Ile Lys Asn Ala Thr Ile Thr Gln Tyr Gln Leu Lys Gly Leu Glu Pro
    690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Gly Lys Met Leu Leu Ile Ala Ile Leu
            740                 745                 750
Gly Ser Ala Gly Met Thr Cys Leu Thr Val Leu Leu Ala Phe Leu Ile
        755                 760                 765
Ile Leu Gln Leu Lys Arg Ala Asn Val Gln Arg Arg Met Ala Gln Ala
    770                 775                 780
Phe Gln Asn Val Arg Glu Glu Pro Ala Val Gln Phe Asn Ser Gly Thr
785                 790                 795                 800
Leu Ala Leu Asn Arg Lys Val Lys Asn Asn Pro Asp Pro Thr Ile Tyr
                805                 810                 815
Pro Val Leu Asp Trp Asn Asp Ile Lys Phe Gln Asp Val Ile Gly Glu
            820                 825                 830
```

```
Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu Pro Val Arg Trp Met Ala Ile Glu
            995                 1000                1005

Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Thr Leu Tyr Glu Lys Phe Thr Tyr
    1100                1105                1110

Ala Gly Ile Asp Cys Ser Ala Glu Glu Ala Ala
    1115                1120

<210> SEQ ID NO 62
<211> LENGTH: 504
<212> TYPE: PRT
<213> ORGANISM: Artificial
<220> FEATURE:
<223> OTHER INFORMATION: Human angiopoietin-2 (ANG-2) with leader and
      His-tag

<400> SEQUENCE: 62

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60
```

```
Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
            245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

Ser Gly His His His His His His
        500

<210> SEQ ID NO 63
<211> LENGTH: 506
<212> TYPE: PRT
<213> ORGANISM: Artificial
<220> FEATURE:
<223> OTHER INFORMATION: Human angiopoietin-1 (ANG-1) with leader and
      His-tag

<400> SEQUENCE: 63

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

```
Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
        370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
            450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe Ser Gly His His His His His
            500                 505
```

ANTIBODIES AGAINST HUMAN ANGIOPOIETIN 2

PRIORITY TO RELATED APPLICATION(S)

This application is a divisional application of U.S. application Ser. No. 12/635,825, filed Dec. 11, 2009, now U.S. Pat. No. 8,133,979, which claims the benefit of European Patent Application No. 08021835.7, filed Dec. 16, 2008. The entire contents of the above-identified applications are hereby incorporated by reference.

The present invention relates to antibodies against human Angiopoietin 2 (anti-ANG-2 antibodies), methods for their production, pharmaceutical compositions containing said antibodies, and uses thereof.

BACKGROUND OF THE INVENTION

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, In: Pathobiology of ocular disease, A dynamic approach, Garner, A., and Klintworth, G. K. (eds.), 2nd edition, Marcel Dekker, New York (1994), pp 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner, N., et al., N. Engl. J. Med. 324 (1991) 1-8; Horak, E. R., et al., Lancet 340 (1992) 1120-1124; and Macchiarini, P., et al., Lancet 340 (1992) 145-146).

ANG-2 and Anti-ANG-2 Antibodies

Human angiopoietin-2 (ANG-2) (alternatively abbreviated with ANGPT2 or ANG2) (SEQ ID No: 107) is described in Maisonpierre, P. C., et al., Science 277 (1997) 55-60 and Cheung, A. H., et al, Genomics 48 (1998) 389-91. The angiopoietins-1 and -2 (ANG-1 (SEQ ID No: 108) and ANG-2 (SEQ ID No: 107) were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family.

Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J Biol Chem 274 (1999), 26523-28. ANG-1 and ANG-2 were originally identified in tissue culture experiments as agonist and antagonist, respectively (see for ANG-1: Davies, S., et al., Cell, 87 (1996) 1161-1169; and for ANG-2: Maisonpierre, P. C., et al., Science 277 (1997) 55-60). All of the known angiopoietins bind primarily to Tie2, and both Ang-1 and -2 bind to Tie2 with an affinity of 3 nM (Kd). Maisonpierre, P. C., et al., Science 277 (1997) 55-60. Ang-1 was shown to support EC survival and to promote endothelium integrity, Davis, S., et al., Cell, 87 (1996) 1161-1169; Kwak, H. J., et al., FEBS Lett 448 (1999) 249-53; Suri, C., et al., Science 282 (1998) 468-71; Thurston, G., et al., Science 286 (1999) 2511-14; Thurston, G., et al., Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al., Science 277 (1997) 55-60. However, many studies of ANG-2 function have suggested a more complex situation. ANG-2 might be a complex regulator of vascular remodeling that plays a role in both vessel sprouting and vessel regression. Supporting such roles for ANG-2, expression analyses reveal that ANG-2 is rapidly induced, together with VEGF, in adult settings of angiogenic sprouting, whereas ANG-2 is induced in the absence of VEGF in settings of vascular regression. Holash, J., et al., Science 284 (1999) 1994-98; Holash, J., et al., Oncogene 18 (1999) 5356-62. Consistent with a context-dependent role, ANG-2 specifically binds to the same endothelial-specific receptor, Tie-2, which is activated by Ang-1, but has context-dependent effects on its activation. Maisonpierre, P. C., et al., Science 277 (1997) 55-60.

Corneal angiogenesis assays have shown that both ANG-1 and ANG-2 had similar effects, acting synergistically with VEGF to promote growth of new blood vessels. Asahara, T., et al., Circ. Res., 83, (1998) 233-40. The possibility that there was a dose-dependent endothelial response was raised by the observation that in vitro at high concentration, ANG-2 can also be pro-angiogenic. Kim, I., et al., Oncogene 19 (2000) 4549-52. At high concentration, ANG-2 acts as an apoptosis survival factor for endothelial cells during serum deprivation apoptosis through activation of Tie2 via PI-3 Kinase and Akt pathway. Kim, I., et al., Oncogene 19 (2000) 4549-52.

Other in vitro experiments suggested that during sustained exposure, the effects of ANG-2 may progressively shift from that of an antagonist to an agonist of Tie2, and at later time points, it may contribute directly to vascular tube formation and neovessel stabilization. Teichert-Kuliszewska, K., et al., Cardiovasc. Res. 49 (2001) 659-70. Furthermore, if ECs were cultivated on fibrin gel, activation of Tie2 with ANG-2 was also observed, perhaps suggesting that the action of ANG-2 could depend on EC differentiation state. Teichert-Kuliszewska; K., et al., Cardiovasc. Res. 49 (2001) 659-70. In microvascular EC cultured in a three-dimensional collagen gel, ANG-2 can also induce Tie2 activation and promote formation of capillary-like structures. Mochizuki, Y., et al., J. Cell. Sci. 115 (2002) 175-83. Use of a 3-D spheroidal coculture as an in-vitro model of vessel maturation demonstrated that direct contact between ECs and mesenchymal cells abrogates responsiveness to VEGF, whereas the presence of VEGF and ANG-2 induced sprouting. Korff, T., et al., Faseb J. 15 (2001) 447-57. Etoh, T., et al. demonstrated that ECs that constitutively express Tie2, the expression of MMP-1, -9 and u-PA were strongly upregulated by ANG-2 in the presence of VEGF. Etoh, T., et al., Cancer Res. 61 (2001) 2145-53. With an in vivo pupillary membrane model, Lobov, I. B., et al. showed that ANG-2 in the presence of endogenous VEGF promotes a rapid increase in capillary diameter, remodeling of the basal lamina, proliferation and migration of endothelial cells, and stimulates sprouting of new blood vessels. Lobov, I. B., et al., Proc. Natl. Acad. Sci. USA 99 (2002) 11205-10. By contrast, ANG-2 promotes endothelial cell death and vessel regression without endogenous VEGF. Lobov, I. B., et al., Proc. Natl. Acad. Sci. USA 99 (2002) 11205-10. Similarly, with an in vivo tumor model, Vajkoczy, P., et al. demonstrated that multicellular aggregates initiate vascular growth by angiogenic sprouting via the simultaneous expression of VEGFR-2 and ANG-2 by host and tumor endothelium. Vajkoczy, P., et al., J. Clin. Invest. 109 (2002) 777-85. This model illustrated that the established microvasculature of growing tumors is characterized by a continuous remodeling, putatively mediated by the expression of VEGF and ANG-2. Vajkoczy, M. A., et al., J Clin. Invest. 09 (2002) 777-85.

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont, D. J., et al., Genes & Development, 8 (1994) 1897-1909; Sato, T. N., Nature, 376 (1995) 70-74; (Thurston, G., et al., Nature Medicine 6 (2000) 460-463). The role of Angiopoietin-1 is thought to be conserved in the adult, where it is expressed widely and constitutively (Hanahan, D., Science, 277 (1997) 48-50; Zagzag, D., et al., Exp Neurology, 159 (1999) 391-400). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, D., 1997; Holash, J., et al., Orzcogerze 18 (1999) 5356-62; Maisonpierre, P. C., 1997). Studies of Angiopoietin-2 expression in pathological angiogenesis have found many tumor types to show vascular Angiopoietin-2 expression (Maisonpierre, P. C., et al., Science 277 (1997) 55-60). Functional studies suggest Angiopoietin-2 is involved in tumor angiogenesis and associate Angiopoietin-2 overexpression with increased tumor growth in a mouse xenograft model (Ahmad, S. A., et al., Cancer Res., 61 (2001)1255-1259). Other studies have associated Angiopoietin-2 overexpression with tumor hypervascularity (Etoh, T., et al., Cancer Res. 61 (2001) 2145-53; Tanaka, F., et al., Cancer Res. 62 (2002) 7124-29).

In recent years Angiopoietin-1, Angiopoietin-2 and/or Tie-2 have been proposed as possible anti-cancer therapeutic targets. For example U.S. Pat. No. 6,166,185, U.S. Pat. No. 5,650,490 and U.S. Pat. No. 5,814,464 each disclose anti-Tie-2 ligand and receptor antibodies. Studies using soluble Tie-2 were reported to decrease the number and size of tumors in rodents (Lin, P, 1997; Lin, P., 1998). Siemester, G., et al. (1999) generated human melanoma cell lines expressing the extracellular domain of Tie-2, injected these into nude mice and reported soluble Tie-2 to result in significant inhibition of tumor growth and tumor angiogenesis. Given both Angiopoietin-1 and Angiopoietin-2 bind to Tie-2, it is unclear from these studies whether Angiopoietin-1, Angiopoietin-2 or Tie-2 would be an attractive target for anti-cancer therapy. However, effective anti-Angiopoietin-2 therapy is thought to be of benefit in treating diseases such as cancer, in which progression is dependant on aberrant angiogenesis where blocking the process can lead to prevention of disease advancement (Folkman, J., Nature Medicine. 1, (1995) 27-31.

In addition some groups have reported the use of antibodies and peptides that bind to Angiopoietin-2. See, for example, U.S. Pat. No. 6,166,185 and US 2003/10124129. WO 03/030833, WO 2006/068953, WO 03/057134 or US 2006/0122370.

Study of the effect of focal expression of Angiopoietin-2 has shown that antagonizing the Angiopoietin-1/Tie-2 signal loosens the tight vascular structure thereby exposing ECs to activating signals from angiogenesis inducers, e.g. VEGF (Hanahan, 1997). This pro-angiogenic effect resulting from inhibition of Angiopoietin-1 indicates that anti-Angiopoietin-1 therapy would not be an effective anti-cancer treatment.

ANG-2 is expressed during development at sites where blood vessel remodeling is occurring. Maisonpierre, P. C., et al., Science 277 (1997) 55-60. In adult individuals, ANG-2 expression is restricted to sites of vascular remodeling as well as in highly vascularized tumors, including glioma, Osada, H., et al., Int. J. Oncol. 18 (2001) 305-09; Koga, K., et al., Cancer Res. 61 (2001) 6248-54, hepatocellular carcinoma, Tanaka, S., et al, J. Clin. Invest. 103 (1999) 341-45, gastric carcinoma, Etoh, T., et al., Cancer Res. 61 (2001) 2145-53; Lee, J. H., et al, Int. J. Oncol. 18 (2001) 355-61, thyroid tumor, Bunone, G., et al., Am J Pathol 155 (1999) 1967-76, non-small cell lung cancer, Wong, M. P., et al., Lung Cancer 29 (2000) 11-22, and cancer of colon, Ahmad, S. A., et al., Cancer 92 (2001) 1138-43, and prostate Wurmbach, J. H., et al., Anticancer Res. 20 (2000) 5217-20. Some tumor cells are found to express ANG-2. For example, Tanaka, S., et al., J. Clin. Invest. 103 (1999) 341-45 detected ANG-2 mRNA in 10 out of 12 specimens of human hepatocellular carcinoma (HCC). Ellis' group reported that ANG-2 is expressed ubiquitously in tumor epithelium. Ahmad, S. A., et al., Cancer 92 (2001) 1138-43. Other investigators reported similar findings. Chen, L., et al., J. Tongji Med. Univ. 21 (2001) 228-30, 235 (2001). By detecting ANG-2 mRNA levels in archived human breast cancer specimens, Sfilogoi, C., et al., Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al., Cancer Res. 62 (2002) 7124-29. However, they found no significant correlation between Ang-1 expression and the microvessel density. Tanaka, F., et al., Cancer Res. 62 (2002) 7124-29. These results suggest that ANG-2 is an indicator of poor prognosis patients with several types of cancer.

Recently, using an ANG-2 knockout mouse model, Yancopoulos' group reported that ANG-2 is required for postnatal angiogenesis. Gale, N. W., et al., Dev. Cell 3 (2002) 411-23. They showed that the developmentally programmed regression of the hyaloid vasculature in the eye does not occur in the ANG-2 knockout mice and their retinal blood vessels fail to sprout out from the central retinal artery. Gale, N. W., et al., Dev. Cell 3 (2002) 411-23. They also found that deletion of ANG-2 results in profound defects in the patterning and function of the lymphatic vasculature. Gale, N. W., et al., Dev. Cell 3 (2002) 411-23. Genetic rescue with Ang-1 corrects the lymphatic, but not the angiogenesis defects. Gale, N. W., et al., Dev. Cell 3 (2002) 411-23.

Peters and his colleagues reported that soluble Tie2, when delivered either as recombinant protein or in a viral expression vector, inhibited in vivo growth of murine mammary carcinoma and melanoma in mouse models. Lin, P., et al., Proc. Natl. Acad. Sci. USA 95 (1998) 8829-34; Lin, P., et al., J. Clin. Invest. 100 (1997) 2072-78. Vascular densities in the tumor tissues so treated were greatly reduced. In addition, soluble Tie2 blocked angiogenesis in the rat corneal stimulated by tumor cell conditioned media. Lin, P., et al., J. Clin. Invest. 100 (1997) 2072-78. Furthermore, Isner and his team demonstrated that addition of ANG-2 to VEGF promoted significantly longer and more circumferential neovascularity than VEGF alone. Asahara, T., et al., Circ. Res., 83 (1998) 233-40. Excess soluble Tie2 receptor precluded modulation of VEGF-induced neovascularization by ANG-2. Asahara, T., et al., Circ. Res., 83, (1998) 233-40. Siemeister, G., et al., Cancer Res. 59 (1999) 3185-91 showed with nude mouse xenografts that overexpression of the extracellular ligand-binding domains of either Flt-1 or Tie2 in the xenografts results in significant inhibition of pathway could not be compensated by the other one, suggesting that the VEGF receptor pathway and the Tie2 pathway should be considered as two independent mediators essential for the process of in vivo angiogenesis. Siemeister, G., et al., Cancer Res. 59 (1999) 3185-91. This is proven by a more recent publication by White, R. R., et al., Proc. Natl. Acad. Sci. USA 100 (2003) 5028-33. In their study, it was demonstrated that a nuclease-resistant RNA aptamer that specifically binds and inhibits ANG-2 significantly inhibited neovascularization induced by bFGF in the rat corneal micropocket angiogenesis model.

SUMMARY OF THE INVENTION

The present invention relates in part to an antibody which binds specifically to human angiopoietin-2 (ANG-2), wherein said antibody comprises, as a heavy chain variable domain CDR3 region, a CDR3 region selected from the group consisting of: SEQ ID NO: 1, SEQ ID NO: 9, SEQ ID NO: 17, SEQ ID NO: 25, SEQ ID NO: 33, SEQ ID NO: 41, and SEQ ID NO: 49.

Preferably the antibody comprises:
a) a heavy chain variable domain which comprises:
a CDR3 region selected from the group consisting of: SEQ ID NO: 1, SEQ ID NO: 9, SEQ ID NO: 17, SEQ ID NO: 25, SEQ ID NO: 33, SEQ ID NO: 41, and SEQ ID NO: 49;
a CDR2 region selected from the group consisting of: SEQ ID NO: 2, SEQ ID NO: 10, SEQ ID NO: 18, SEQ ID NO: 26, SEQ ID NO: 34, SEQ ID NO: 42, and SEQ ID NO: 50; and
a CDR1 region selected from the group consisting of: SEQ ID NO: 3, SEQ ID NO: 11, SEQ ID NO: 19, SEQ ID NO: 27, SEQ ID NO: 35, SEQ ID NO: 43, and SEQ ID NO: 51; and
b) the light chain variable domain which comprises:
a CDR3 region selected from the group consisting of: SEQ ID NO: 4, SEQ ID NO: 12, SEQ ID NO: 20, SEQ ID NO: 28, SEQ ID NO: 36, SEQ ID NO: 44, and SEQ ID NO: 52;
a CDR2 region of SEQ ID NO: 5, SEQ ID NO: 13, SEQ ID NO: 21, SEQ ID NO: 29, SEQ ID NO: 37, SEQ ID NO: 45, and SEQ ID NO: 53; and
a CDR1 region selected from the group consisting of: SEQ ID NO: 6, SEQ ID NO: 14, SEQ ID NO: 22, SEQ ID NO: 30, SEQ ID NO: 38, SEQ ID NO: 46, and SEQ ID NO: 54.

Preferably the antibody comprises:
a) a heavy chain variable domain selected from the group consisting of: SEQ ID NO: 7, SEQ ID NO: 15, SEQ ID NO: 23, SEQ ID NO: 31, SEQ ID NO: 39, SEQ ID NO: 47, and SEQ ID NO: 55; and
b) a light chain variable domain selected from the group consisting of: SEQ ID NO: 8, SEQ ID NO: 16, SEQ ID NO: 24, SEQ ID NO: 32, SEQ ID NO: 40, SEQ ID NO: 48, and SEQ ID NO: 56.

Preferably the antibody is characterized in that the antibody does not specifically bind to Angiopoietin 1 (ANG-1).

A further embodiment of the invention is a pharmaceutical composition comprising an antibody according to the invention.

A further embodiment of the invention is the use of an antibody according to the invention for the manufacture of a pharmaceutical composition.

A further embodiment of the invention is the use of an antibody according to the invention for the prevention of metastasis.

A further embodiment of the invention is the use of an antibody according to the invention for the treatment of cancer.

A further embodiment of the invention is the use of an antibody according to the invention for the treatment of vascular diseases.

A further embodiment of the invention is the use of an antibody according to the invention for the treatment of retinopathy.

A further embodiment of the invention is a nucleic acid encoding a heavy chain variable domain and/or a light chain variable domain of an antibody according to the invention.

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

The antibodies according to the invention are especially useful for the prevention of secondary tumors/metastasis or in the treatment of vascular diseases such as retinopathies.

DESCRIPTION OF THE AMINO ACID SEQUENCES

SEQ ID NO: 1 heavy chain CDR3, <ANG-2>Ang2i_LC06
SEQ ID NO: 2 heavy chain CDR2, <ANG-2>Ang2i_LC06
SEQ ID NO: 3 heavy chain CDR1, <ANG-2>Ang2i_LC06
SEQ ID NO: 4 light chain CDR3, <ANG-2>Ang2i_LC06
SEQ ID NO: 5 light chain CDR2, <ANG-2>Ang2i_LC06
SEQ ID NO: 6 light chain CDR1, <ANG-2>Ang2i_LC06
SEQ ID NO: 7 heavy chain variable domain, <ANG-2>Ang2i_LC06
SEQ ID NO: 8 light chain variable domain, <ANG-2>Ang2i_LC06
SEQ ID NO: 9 heavy chain CDR3, <ANG-2>Ang2i_LC07
SEQ ID NO: 10 heavy chain CDR2, <ANG-2>Ang2i_LC07
SEQ ID NO: 11 heavy chain CDR1, <ANG-2>Ang2i_LC07
SEQ ID NO: 12 light chain CDR3, <ANG-2>Ang2i_LC07
SEQ ID NO: 13 light chain CDR2, <ANG-2>Ang2i_LC07
SEQ ID NO: 14 light chain CDR1, <ANG-2>Ang2i_LC07
SEQ ID NO: 15 heavy chain variable domain, <ANG-2>Ang2i_LC07
SEQ ID NO: 16 light chain variable domain, <ANG-2>Ang2i_LC07
SEQ ID NO: 17 heavy chain CDR3, <ANG-2>Ang2k_LC08
SEQ ID NO: 18 heavy chain CDR2, <ANG-2>Ang2k_LC08
SEQ ID NO: 19 heavy chain CDR1, <ANG-2>Ang2k_LC08
SEQ ID NO: 20 light chain CDR3, <ANG-2>Ang2k_LC08
SEQ ID NO: 21 light chain CDR2, <ANG-2>Ang2k_LC08
SEQ ID NO: 22 light chain CDR1, <ANG-2>Ang2k_LC08
SEQ ID NO: 23 heavy chain variable domain, <ANG-2>Ang2k_LC08
SEQ ID NO: 24 light chain variable domain, <ANG-2>Ang2k_LC08
SEQ ID NO: 25 heavy chain CDR3, <ANG-2>Ang2s_LC09
SEQ ID NO: 26 heavy chain CDR2, <ANG-2>Ang2s_LC09
SEQ ID NO: 27 heavy chain CDR1, <ANG-2>Ang2s_LC09
SEQ ID NO: 28 light chain CDR3, <ANG-2>Ang2s_LC09
SEQ ID NO: 29 light chain CDR2, <ANG-2>Ang2s_LC09
SEQ ID NO: 30 light chain CDR1, <ANG-2>Ang2s_LC09

SEQ ID NO: 31 heavy chain variable domain, <ANG-2>Ang2s_LC09
SEQ ID NO: 32 light chain variable domain, <ANG-2>Ang2s_LC09
SEQ ID NO: 33 heavy chain CDR3, <ANG-2>Ang2i_LC10
SEQ ID NO: 34 heavy chain CDR2, <ANG-2>Ang2i_LC10
SEQ ID NO: 35 heavy chain CDR1, <ANG-2>Ang2i_LC10
SEQ ID NO: 36 light chain CDR3, <ANG-2>Ang2i_LC10
SEQ ID NO: 37 light chain CDR2, <ANG-2>Ang2i_LC10
SEQ ID NO: 38 light chain CDR1, <ANG-2>Ang2i_LC10
SEQ ID NO: 39 heavy chain variable domain, <ANG-2>Ang2i_LC10
SEQ ID NO: 40 light chain variable domain, <ANG-2>Ang2i_LC10
SEQ ID NO: 41 heavy chain CDR3, <ANG-2>Ang2k_LC11
SEQ ID NO: 42 heavy chain CDR2, <ANG-2>Ang2k_LC11
SEQ ID NO: 43 heavy chain CDR1, <ANG-2>Ang2k_LC11
SEQ ID NO: 44 light chain CDR3, <ANG-2>Ang2k_LC11
SEQ ID NO: 45 light chain CDR2, <ANG-2>Ang2k_LC11
SEQ ID NO: 46 light chain CDR1, <ANG-2>Ang2k_LC11
SEQ ID NO: 47 heavy chain variable domain, <ANG-2>Ang2k_LC11
SEQ ID NO: 48 light chain variable domain, <ANG-2>Ang2k_LC11
SEQ ID NO: 49 heavy chain CDR3, <ANG-2>Ang2s_R3_LC03
SEQ ID NO: 50 heavy chain CDR2, <ANG-2>Ang2s_R3_LC03
SEQ ID NO: 51 heavy chain CDR1, <ANG-2>Ang2s_R3_LC03
SEQ ID NO: 52 light chain CDR3, <ANG-2>Ang2s_R3_LC03
SEQ ID NO: 53 light chain CDR2, <ANG-2>Ang2s_R3_LC03
SEQ ID NO: 54 light chain CDR1, <ANG-2>Ang2s_R3_LC03
SEQ ID NO: 55 heavy chain variable domain, <ANG-2>Ang2s_R3_LC03
SEQ ID NO: 56 light chain variable domain, <ANG-2>Ang2s_R3_LC03
SEQ ID NO: 57 human heavy chain constant region derived from IgG1
SEQ ID NO: 58 human heavy chain constant region derived from IgG4
SEQ ID NO: 59 kappa light chain constant region
SEQ ID NO: 60 lambda light chain constant region
SEQ ID NO: 61 Human Tie-2 receptor
SEQ ID NO: 62 Human angiopoietin-2 (ANG-2) with leader and His-tag
SEQ ID NO: 63 Human angiopoietin-1 (ANG-1) with leader and His-tag

DESCRIPTION OF THE FIGURES

FIG. 8 ANG-1 binding via Biacore sensogramm.
FIG. 9 Prevention of lung metastasis/secondary tumors by the antibodies according to the invention in primary colon tumor xenograft (9A) and primary breast xenograft (9B)
FIG. 10 Inhibition of tethinopaty by the antibodies according to the invention.

DETAILED DESCRIPTION OF THE INVENTION

Figure 1A:
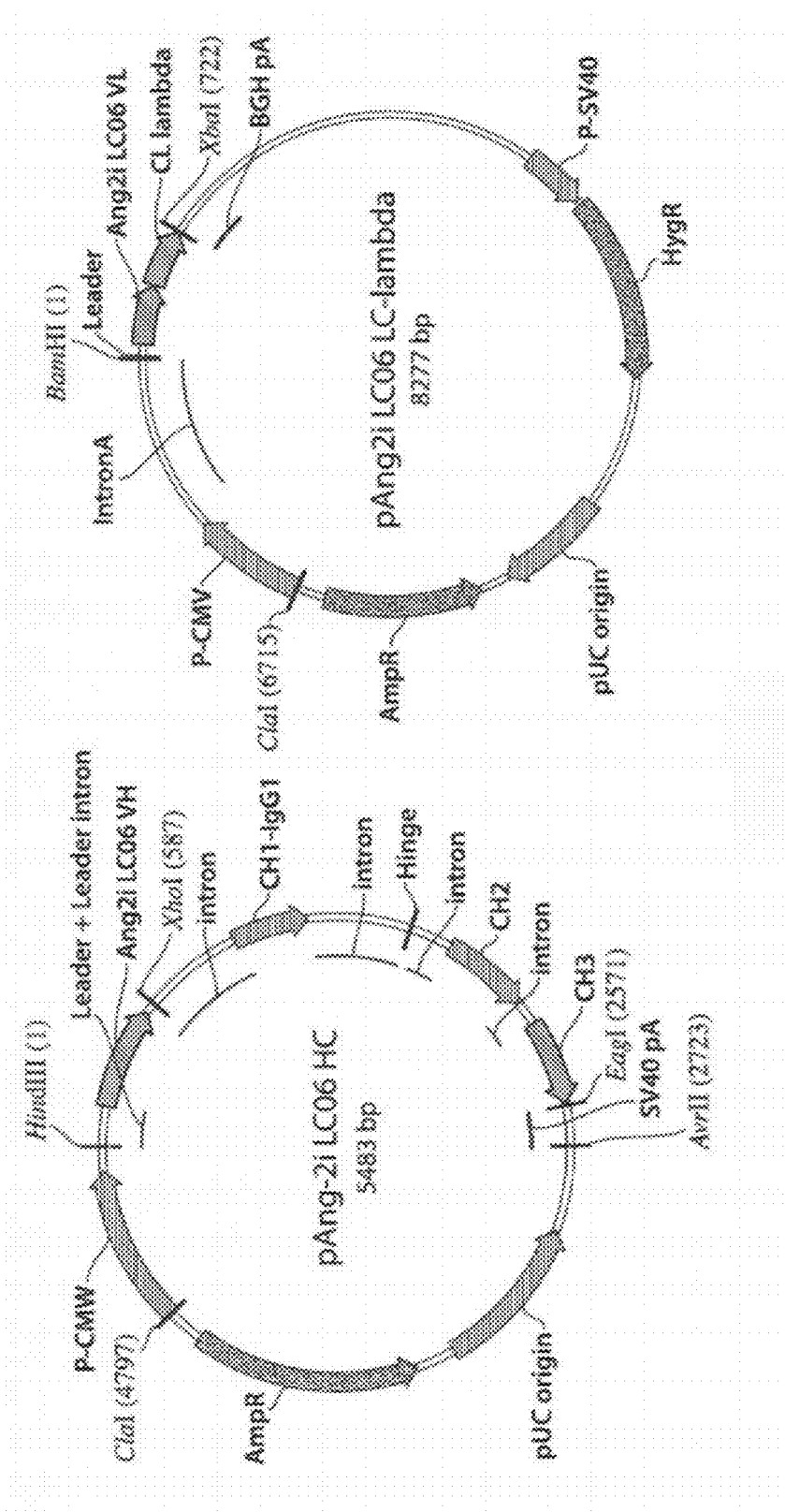
FIG. 1 Cloning of IgGs for transient expressions into expression vectors transient expressions A) Ang2i-LC06 (FIG. 1A) B.) Ang2i-LC06 (FIG. 1B)
FIG. 2 SDS-PAGE Gel of purified anti ANG-2 antibodies Ang2i-LC06, Ang2i-LC07 and Ang2k-LC08
FIG. 3 Angiopoietin-Tie2 interaction ELISA
FIG. 4 Inhibition of ANG-2 binding to Tie2 by Ang2i-LC06 and Ang2k-LC08
FIG. 5 Inhibition of ANG-1 binding to Tie2 by Ang2i-LC06 and Ang2k-LC08
FIG. 6 Colo205 xenograft model to test in vivo efficacy of anti ANG-2 antibodies
FIG. 7 KPL-4 xenograft model to test in vivo efficacy of anti ANG-2 antibodies.

The invention comprises an antibody which binds specifically to human angiopoietin-2 (ANG-2), wherein said antibody comprises, as a heavy chain variable domain CDR3 region, a CDR3 region selected from the group consisting of: SEQ ID NO: 1, SEQ ID NO: 9, SEQ ID NO: 17, SEQ ID NO: 25, SEQ ID NO: 33, SEQ ID NO: 41, and SEQ ID NO: 49.

In one embodiment of the invention the antibody comprises:
a) a heavy chain variable domain which comprises:
  a CDR3 region selected from the group consisting of: SEQ ID NO: 1, SEQ ID NO: 9, SEQ ID NO: 17, SEQ ID NO: 25, SEQ ID NO: 33, SEQ ID NO: 41, and SEQ ID NO: 49;
  a CDR2 region selected from the group consisting of: SEQ ID NO: 2, SEQ ID NO: 10, SEQ ID NO: 18, SEQ ID NO: 26, SEQ ID NO: 34, SEQ ID NO: 42, and SEQ ID NO: 50; and
  a CDR1 region selected from the group consisting of: SEQ ID NO: 3, SEQ ID NO: 11, SEQ ID NO: 19, SEQ ID NO: 27, SEQ ID NO: 35, SEQ ID NO: 43, and SEQ ID NO: 51; and
b) a light chain variable domain which comprises:
  a CDR3 region selected from the group consisting of: SEQ ID NO: 4, SEQ ID NO: 12, SEQ ID NO: 20, SEQ ID NO: 28, SEQ ID NO: 36, SEQ ID NO: 44, and SEQ ID NO: 52;
  a CDR2 region selected from the group consisting of: SEQ ID NO: 5, SEQ ID NO: 13, SEQ ID NO: 21, SEQ ID NO: 29, SEQ ID NO: 37, SEQ ID NO: 45, and SEQ ID NO: 53; and
  a CDR1 region selected from the group consisting of: SEQ ID NO: 6, SEQ ID NO: 14, SEQ ID NO: 22, SEQ ID NO: 30, SEQ ID NO: 38, SEQ ID NO: 46, and SEQ ID NO: 54.

Preferably the antibody comprises:
a) a heavy chain variable domain selected from the group consisting of: SEQ ID NO: 7, SEQ ID NO: 15, SEQ ID NO: 23, SEQ ID NO: 31, SEQ ID NO: 39, SEQ ID NO: 47, and SEQ ID NO: 55; and
b) a light chain variable domain selected from the group consisting of: SEQ ID NO: 8, SEQ ID NO: 16, SEQ ID NO: 24, SEQ ID NO: 32, SEQ ID NO: 40, SEQ ID NO: 48, and SEQ ID NO: 56.

Another embodiment of the invention is an antibody which binds specifically to human ANG-2, which is characterized in that the antibody is does not specifically bind to human Angiopoietin 1 (ANG-1). Typical antibodies which specifically bind to human ANG-2, but not to human ANG-1 are e.g. Ang2s_R3_LC03, Ang2s_LC09, Ang2i_LC06, Ang2i_LC07, and antibodies binding to the same epitope as Ang2s_R3_LC03, Ang2s_LC09, Ang2i_LC06, Ang2i_LC07, and Ang2i_LC10. Preferred such antibodies are those which bind to the same epitope as Ang2i_LC06. Therefore, in one embodiment of the invention, the antibody binds specifically to human angiopoietin-2 (ANG-2) but not to human ANG-1 binds to the same epitope as Ang2s_R3_LC03, Ang2s_LC09, Ang2i_LC06, Ang2i_LC07, or Ang2i_LC10, and preferably to the same epitope as Ang2i_LC06. Such antibodies bind specifically to ANG-2, but not to ANG-1 can have improved properties such as efficacy, less toxicity, pharmacokinetic properties compared to ANG-2 and ANG-1 specific antibodies.

Therefore in one embodiment of the invention the antibody is one which binds specifically to human angiopoietin-2 (ANG-2) but not to human ANG-1 and comprises:
a) a heavy chain variable domain which comprises:
a CDR3 region selected from the group consisting of: SEQ ID NO: 1, SEQ ID NO: 9, SEQ ID NO: 25, SEQ ID NO: 33, and SEQ ID NO: 49;
a CDR2 region selected from the group consisting of: SEQ ID NO: 2, SEQ ID NO: 10, SEQ ID NO: 26, SEQ ID NO: 34, and SEQ ID NO: 50; and
a CDR1 region selected from the group consisting of: SEQ ID NO: 3, SEQ ID NO: 11, SEQ ID NO: 27, SEQ ID NO: 35, and SEQ ID NO: 51; and
b) a light chain variable domain which comprises:
a CDR3 region selected from the group consisting of: SEQ ID NO: 4, SEQ ID NO: 12, SEQ ID NO: 28, SEQ ID NO: 36, and SEQ ID NO: 52;
a CDR2 region selected from the group consisting of: SEQ ID NO: 5, SEQ ID NO: 13, SEQ ID NO: 29, SEQ ID NO: 37, and SEQ ID NO: 53; and
a CDR1 region selected from the group consisting of: SEQ ID NO: 6, SEQ ID NO: 14, SEQ ID NO: 30, SEQ ID NO: 38, and SEQ ID NO: 54.
Preferably the antibody binds specifically to human angiopoietin-2 (ANG-2) but not to human ANG-1 and comprises:
a) a heavy chain variable domain selected from the group consisting of: SEQ ID NO: 7, SEQ ID NO: 15, SEQ ID NO: 31, SEQ ID NO: 39, and SEQ ID NO: 55; and
b) q light chain variable domain selected from the group consisting of: SEQ ID NO: 8, SEQ ID NO: 16, SEQ ID NO: 32, SEQ ID NO: 40, and SEQ ID NO: 56.
In one embodiment said antibody according to the invention comprises:
a) a heavy chain variable domain which comprises a CDR3 region of SEQ ID NO: 1 or SEQ ID NO: 9, a CDR2 region of SEQ ID NO: 2 or SEQ ID NO: 10, and a CDR1 region of SEQ ID NO: 3 or SEQ ID NO: 11, and
b) a light chain variable domain which comprises a CDR3 region of SEQ ID NO: 4 or SEQ ID NO: 12, a CDR2 region of SEQ ID NO: 5 or SEQ ID NO: 13, and a CDR1 region of SEQ ID NO: 6 or SEQ ID NO: 14.
In one embodiment the antibody according to the invention comprises:
a) a heavy chain variable domain of SEQ ID NO: 7 or SEQ ID NO: 15; and
b) a light chain variable domain of SEQ ID NO: 8 or SEQ ID NO: 16.
In one embodiment the antibody according to the invention comprises:
a) a heavy chain variable domain which comprises a CDR3 region of SEQ ID NO: 1, a CDR2 region of SEQ ID NO: 2, and a CDR1 region of SEQ ID NO: 3, and
b) a light chain variable domain which comprises a CDR3 region of SEQ ID NO: 4, a CDR2 region of SEQ ID NO: 5, and a CDR1 region of SEQ ID NO: 6.
In one embodiment the antibody according to the invention comprises:
a) a heavy chain variable domain of SEQ ID NO: 7; and
b) a light chain variable domain of SEQ ID NO: 8.
In one embodiment the antibody according to the invention comprises:
a) a heavy chain variable domain which comprises a CDR3 region of SEQ ID NO: 17, a CDR2 region of SEQ ID NO: 18, and a CDR1 region of SEQ ID NO: 19, and
b) a light chain variable domain which comprises a CDR3 region of SEQ ID NO: 20, a CDR2 region of SEQ ID NO: 21, and a CDR1 region of SEQ ID NO: 22.
In one embodiment the antibody according to the invention comprises:
a) a heavy chain variable domain of SEQ ID NO: 23; and
b) a light chain variable domain of SEQ ID NO: 24.
Preferably the antibody according to the invention is of human IgG1 subclass or is of human IgG4 subclass.

The term "antibody" encompasses the various forms of antibody structures including but not being limited to whole antibodies and antibody fragments, The antibody according to the invention is preferably a humanized antibody, chimeric antibody, or further genetically engineered antibody, as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules (scFv or scFab), and multispecific antibodies (e.g. bispecific) formed from antibody fragments. scFv antibodies are, e.g. described in Houston, J. S., Methods in Enzymol. 203 (1991) 46-88). In addition, antibody fragments comprise single chain polypeptides having the characteristics of a $V_H$ domain, namely being able to assemble together with a $V_L$ domain, or of a $V_L$ domain binding to ANG-2, namely being able to assemble together with a $V_H$ domain to a functional antigen binding site and thereby providing the property. ScFvs can be stabilized using e.g. a) disulfide stabilization (see e.g. in WO 94/029350, Rajagopal, V., et al., Prot. Engin. (1997) 1453-59; Kobayashi, H., et al., Nuclear Medicine & Biology, Vol. 25, (1998) 387-393; or Schmidt, M., et al., Oncogene (1999) 18 1711-1721.) or b) stabilized frameworks (e.g. by specific mutations of the see e.g. WO 2007/109254 specific stabilized frameworks see e.g. U.S. Pat. No. 7,258,985, Furrer, F., et al., Invest. Ophthalmol. Vis. Sci. 50 (2009), pp. 771-778 or Ottiger, M., et al., Invest. Ophthalmol. Vis. Sci. 50 (2009), pp. 779-786.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See e.g. Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, S. P. C., et al., and Boerner, et al. are also available for the preparation of human monoclonal antibodies (Cole, S. P. C., et al., Monoclonal Antibodies and Cancer Therapy, Liss, A. R., (1985) 77-96; and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain ($V_L$), variable domain of a heavy chain ($V_H$) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat, E. A., et al., Sequences of Proteins of Immunological Interest, 5th ed., Public Health Service, National Institutes of Health, Bethesda, Md. (1991) and/or those residues from a "hypervariable loop."

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operable linked to DNA for a polypeptide if it is expressed as a preprotein that participates in the secretion of the polypeptide; a promoter or enhancer is operable linked to a coding sequence if it affects the transcription of the sequence; or a ribosome binding site is operable linked to a coding sequence if it is positioned so as to facilitate translation. Generally, "operably linked" means that the DNA sequences being linked are collinear, and, in the case of a secretory leader, contiguous and in reading frame. However, enhancers do not have to be contiguous Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

As used herein, the terms "bind", "binds", and "binding" refer to the binding of the antibody to an epitope of an antigen in an in vitro assay, preferably in an plasmon resonance assay (BIAcore, GE-Healthcare Uppsala, Sweden) (Example 3) with purified wild-type ANG-2 antigen. The affinity of the binding is defined by the terms ka (rate constant for the association of the antibody from the antibody/antigen complex), $k_D$ (dissociation constant), and $K_D$ ($k_D$/ka). Binding means a binding affinity ($K_D$) of $10^{-8}$ mol/l or less, preferably $10^{-9}$ M to $10^{-13}$ mol/l.

Binding of the antibody to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

As used herein, the term "not binding to ANG-1" denotes that the antibody has an EC50-value above 8000 ng/ml in an in vitro ANG-1 binding ELISA assay (according to Example 2).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boakle, R. J., et al., Nature 282 (1975) 742-743, Lukas, T. J., et al., J. Immunol. 127 (1981) 2555-2560, Brunhouse, R., and Cebra, J. J., Mol. Immunol. 16 (1979) 907-917, Burton, D. R., et al., Nature 288 (1980) 338-344, Thommesen, J. E., et al., Mol. Immunol. 37 (2000) 995-1004, Idusogie, E. E., et al., J. Immunol. 164 (2000) 4178-4184, Hezareh, M., et al., J. Virology 75 (2001) 12161-12168, Morgan, A., et al., Immunology 86 (1995) 319-324, EP 0307434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation and C1q and C3 binding, whereas IgG4 do not activate the complement system and do not bind C1q and C3.

The antibody according to the invention preferably comprises a Fc part from human origin which is Fc part of a human antibody of the subclass IgG1.

The antibody according to the invention is characterized in that the constant chains are of human origin. Such constant chains are well known in the state of the art and e.g. described by Kabat, E. A. (see e.g. Johnson, G. and Wu, T. T., Nucleic Acids Res. 28 (2000) 214-218). For example, a useful human heavy chain constant region comprises an amino acid sequence of SEQ ID NO: 57 or of SEQ ID NO: 58. For example, a useful human light chain constant region comprises an amino acid sequence of a kappa-light chain constant region of SEQ ID NO: 59, or of a lambda-light chain constant region of SEQ ID NO: 60.

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain lc region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the monospecific bivalent parent antibody is in regard to FcR binding of IgG4 subclass or of IgG1 or IgG2 subclass with a mutation in S228, L234, L235 and/or D265, and/or contains the PVA236 mutation. In one embodiment the mutations in the monospecific bivalent parent antibody are S228P, L234A, L235A, L235E and/or PVA236. In another embodiment the mutations in the monospecific bivalent parent antibody are in IgG4 S228P and in IgG1 L234A and L235A. Constant heavy chain regions shown in SEQ ID NO: 57 and 58. In one embodiment the constant heavy chain region of the monospecific bivalent parent antibody is of SEQ ID NO: 57 with mutations L234A and L235A. In another embodiment the constant heavy chain region of the monospecific bivalent parent antibody is of SEQ ID NO: 58 with mutation S228P. In another embodiment the constant light chain region of the monospecific bivalent parent antibody is a kappa light chain region of SEQ ID NO: 59, or a lambda light chain constant region of SEQ ID NO: 60. In one embodiment of the invention the constant heavy chain region of the monospecific bivalent parent antibody is of SEQ ID NO: 57 or of SEQ ID NO: 58 with mutation S228P.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of CCR5 expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., J. Drug Res. 48 (1998) 870-880.

The antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the antibody according to the invention are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenylsepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A. Appl. Biochem. Biotech. 75 (1998) 93-102).

The invention comprises a method for the treatment of a patient in need of therapy, characterized by administering to the patient a therapeutically effective amount of an antibody according to the invention.

The invention comprises the use of an antibody according to the invention for therapy.

The invention comprises the use of an antibody according to the invention for the preparation of a medicament for the prevention of metastasis.

The invention comprises the use of an antibody according to the invention for the preparation of a medicament for the treatment of cancer.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

Another aspect of the invention is said pharmaceutical composition for the prevention of metastasis.

Another aspect of the invention is an antibody according to the invention for the prevention of metastasis.

Another aspect of the invention is the use of an antibody according to the invention for the manufacture of a medicament for the prevention of metastasis.

Another aspect of the invention is a method of prevention metastasis in patient suffering from primary cancer by administering an antibody according to the invention to a patient in the need of such preventative treatment.

We could show highly efficient prevention of spotanouenes metastasis/secondary tumors in vivo in a orthotopic and a subcutaneous cancer model (see Example 9) (in contrast to experimental model where the tumor cells are injected i.v. This is similar to the clinical situation wherein cells disseminate from a primary tumor and metastase to secondary organ like lung or liver (where secondary tumors).

The term "metastasis" according to the invention refers to the transmission of cancerous cells from the primary tumor to one or more sites elsewhere in a patient where then secondary tumors develop. MetastasMeans to determine if a cancer has metastasized are known in the art and include bone scan, chest X-ray, CAT scan, MRI scan, and tumor marker tests.

The term "prevention of metastasis" or "prevention of secondary tumors" as used herein have the same meaning and refers a prophylactic agent against metastasis in patient suffering from relapsed HER2 positive cancer in this way inhibiting or reducing a further transmission of cancerous cells from the primary tumor to one or more sites elsewhere in a patient. This means that the metastasis of the primary, tumor or cancer is prevented, delayed, or reduced and thus the development of secondary tumors is prevented, delayed, or reduced. Preferably the metastasis i.e secondary tumors of the lung are prevented or reduced, which means that metastatic transmission of cancerous cells from the primary tumor to the lung is prevented or reduced.

Another aspect of the invention is said pharmaceutical composition for the treatment of cancer.

Another aspect of the invention is an antibody according to the invention for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Another aspect of the invention is said pharmaceutical composition as anti-angiogenic agent. Such anti-angiogenic agent can be used for the treatment of cancer, especially solid tumors, and other vascular diseases.

Another aspect of the invention is the use of an antibody according to the invention for the manufacture of a medicament for the treatment of vascular diseases.

Another aspect of the invention is an antibody according to the invention for the treatment of vascular diseases.

A preferred embodiment is an antibody according to the invention for the treatment of retinopathy.

A preferred embodiment is the use of an antibody according to the invention for the manufacture of a medicament for the treatment of retinopathy Another aspect of the invention is method of treatment of patient suffering from vascular diseases by administering an antibody according to the invention to a patient in the need of such treatment.

The term "vascular diseases" includes Cancer, Inflammatory diseases, Atherosclerosis, Ischemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes (such as proliferative retinopathies or age-related macular degeneration (AMD)), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, In: Pathobiology of ocular disease, A dynamic approach, Garner, A., and Klintworth, G. K. (eds.), 2nd edition, Marcel Dekker, New York (1994), pp 1625-1710).

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al, PNAS. 69 (1972) 7110ff.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Experimental Procedure 1

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies variants of expression plasmids for transient expression (e.g. in HEK293 EBNA or HEK293-F cells) or for stable expression (e.g. in CHO cells) based either on a cDNA organization with a CMV-Intron A promoter or on a genomic organization with a CMV promoter (e.g. FIG. 1) were applied.

Beside the antibody expression cassette the vectors contained:
 an origin of replication which allows replication of this plasmid in *E. coli*, and
 a β-lactamase gene which confers ampicillin resistance in *E. coli*.

The transcription unit of the antibody gene is composed of the following elements:
 unique restriction site(s) at the 5' end
 the immediate early enhancer and promoter from the human cytomegalovirus,
 followed by the Intron A sequence in the case of the cDNA organization,
 a 5'-untranslated region of a human antibody gene,
 a immunoglobulin heavy chain signal sequence,
 the human antibody chain (heavy chain, modified heavy chain or light chain) either as cDNA or as genomic organization with an the immunoglobulin exon-intron organization
 a 3' untranslated region with a polyadenylation signal sequence, and
 unique restriction site(s) at the 3' end.

The fusion genes comprising the heavy chain sequences of the selected antibody as described below were generated by PCR and/or gene synthesis and assembled with known recombinant methods and techniques by connection of the according nucleic acid segments e.g. using unique NsiI and EcoRI sites in the genomic heavy chain vectors. The subcloned nucleic acid sequences were verified by DNA sequencing. For transient and stable transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

Antibodies were generated by transient transfection of the two plasmids encoding the heavy or modified heavy chain, respectively and the corresponding light chain using the HEK293-F system (Invitrogen) according to the manufacturer's instruction. Briefly, HEK293-F cells (Invitrogen) growing in suspension either in a shake flask or in a stirred fermenter in serumfree FreeStyle 293 expression medium (Invitrogen) were transfected with a mix of the two respective expression plasmids and 293fectin or fectin (Invitrogen). For e.g. 2 L shake flask (Corning) HEK293-F cells were seeded at a density of 1.0 E*6 cells/mL in 600 mL and incubated at 120 rpm, 8% CO2. The day after the cells were transfected at a cell density of ca. 1.5 E*6 cells/mL with ca. 42 mL mix of A) 20 mL Opti-MEM (Invitrogen) with 600 µg total plasmid DNA (1 µg/mL) encoding the heavy or modified heavy chain, respectively and the corresponding light chain in an equimolar ratio and B) 20 ml Opti-MEM+1.2 mL 293 fectin or fectin (2 µl/mL). According to the glucose consumption glucose solution was added during the course of the fermentation. The supernatant containing the secreted antibody was harvested after 5-10 days and antibodies were either directly purified from the supernatant or the supernatant was frozen and stored.

Protein Determination

The protein concentration of purified antibodies and derivatives was determined by determining the optical density (OD) at 280 nm, using the molar extinction coefficient calculated on the basis of the amino acid sequence according to Pace, C. N., et. al., Protein Science, 4 (1995), 2411-1423.

Antibody Concentration Determination in Supernatants

The concentration of antibodies and derivatives in cell culture supernatants was estimated by immunoprecipitation with Protein A Agarose-beads (Roche). 60 μL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon) once with 0.5 mL TBS-NP40, twice with 0.5 mL 2× phosphate buffered saline (2×PBS, Roche) and briefly four times with 0.5 mL 100 mM Na-citrate pH 5.0. Bound antibody is eluted by addition of 35 μl NuPAGE® LDS Sample Buffer (Invitrogen). Half of the sample is combined with NuPAGE® Sample Reducing Agent or left unreduced, respectively, and heated for 10 min at 70° C. Consequently, 20 μl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was measured by Protein A-HPLC chromatography. Briefly, cell culture supernatants containing antibodies and derivatives that bind to Protein A were applied to a HiTrap Protein A column (GE Healthcare) in 50 mM K2HPO4, 300 mM NaCl, pH 7.3 and eluted from the matrix with 50 mM acetic acid, pH 2.5 on a Dionex HPLC-System. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 μL/well biotinylated anti-human IgG capture molecule F(ab')2<h-Fcγ>B1 (Dianova) at 0.1 μg/mL for 1 h at room temperature or alternatively over night at 4° C. and subsequently washed three times with 200 μL/well PBS, 0.05% Tween (PBST, Sigma). 100 μL/well of a dilution series in PBS (Sigma) of the respective antibody containing cell culture supernatants was added to the wells and incubated for 1-2 h on a microtiterplate shaker at room temperature. The wells were washed three times with 200 μL/well PBST and bound antibody was detected with 100 μl F(ab')2<hFcgamma>POD (Dianova) at 0.1 μg/mL as detection antibody for 1-2 h on a microtiterplate shaker at room temperature. Unbound detection antibody was washed away three times with 200 μL/well PBST and the bound detection antibody was detected by addition of 100 μL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE Healthcare) and washed with PBS. Elution of antibodies was achieved at acidic pH followed by immediate neutralization of the sample. Aggregated protein was separated from monomeric antibodies by size exclusion chromatography (Superdex 200, GE Healthcare) in 20 mM Histidine, 140 mM NaCl pH 6.0. Monomeric antibody fractions were pooled, concentrated if required using e.g. a MILLIPORE Amicon Ultra (30 MWCO) centrifugal concentrator and stored at −80° C. Part of the samples were provided for subsequent protein analytics and analytical characterization e.g. by SDS-PAGE, size exclusion chromatography, mass spectrometry and Endotoxin determination (see FIG. 2).

SDS-PAGE

The NuPAGE® Pre-Cast gel system (Invitrogen) was used according to the manufacturer's instruction. In particular, 4-20% NuPAGE® Novex® TRIS-Glycine Pre-Cast gels and a Novex® TRIS-Glycine SDS running buffer were used. (see e.g. FIG. 1). Reducing of samples was achieved by adding NuPAGE® sample reducing agent prior to running the gel.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Dionex HPLC system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of antibodies was determined and confirmed via electrospray ionization mass spectrometry (ESI-MS). Briefly, 100 μg purified antibodies were deglycosylated with 50 mU N-Glycosidase F (PNGaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 μg antibody in 115 μl were incubated with 60 μl 1M TCEP and 50 μl 8 M Guanidinium-hydrochloride subsequently desalted. The total mass and the mass of the reduced heavy and light chains was determined via ESI-MS on a Q-Star Elite MS system equipped with a NanoMate source.

ANG-1 and ANG-2 Binding ELISA

The binding properties of antibodies directed against ANGPTs (Angiopoietin 1 or 2) were evaluated in an ELISA assay with full-length Angiopoietin-2-His protein (R&D Systems #623-AN/CF or in house produced material) or Angiopoietin-1-His (R&D systems #923-AN). Therefore 96 well plates (Falcon polystyrene clear enhanced microtiter plates or Nunc Maxisorb) were coated with 100 μl 1 μg/mL recombinant human Angiopoietin-1 or Angiopoietin-2 (carrier-free) in PBS (Sigma) for 2 h at room temperature or over night at 4° C. The wells were washed three times with 300 μl PBST (0.2% Tween 20) and blocked with 200 μl 2% BSA 0.1% Tween 20 for 30 min at room temperature and subsequently washed three times with 300 μl PBST. 100 μL/well of a dilution series (40 pM-0.01 pM) of purified test antibody against <ANG-2> and as a reference Mab536 (Oliner, J., et al., Cancer Cell. Nov. 6 (2004) 507-16, US 2006/0122370) in PBS was added to the wells and incubated for 1 h on a microtiterplate shaker at room temperature. The wells were washed three times with 300 μl PBST (0.2% Tween 20) and bound antibody was detected with 100 μL/well 0.1 μg/ml F(ab')<hk>POD (Biozol Cat. No. 206005) in 2% BSA 0.1% Tween 20 as detection antibody for 1 h on a microtiterplate shaker at room temperature. Unbound detection antibody was washed away three times with 300 μL/well PBST and the bound detection antibody was detected by addition of 100 μL ABTS/well. Determination of absorbance was performed on a Tecan Fluor Spectrometer at a measurement wavelength of 405 nm (reference wavelength 492 nm).

ANG-2 Binding BIACORE

Binding of the antibodies to the antigen e.g. human ANG-2 were investigated by surface plasmon resonance using a BIA-CORE T100 instrument (GE Healthcare Biosciences AB, Uppsala, Sweden). Briefly, for affinity measurements goat<hIgG-Fcgamma>polyclonal antibodies were immobilized on a CM4 chip via amine coupling for presentation of the antibodies against human ANG-2. Binding was measured in HBS buffer (HBS-P (10 mM HEPES, 150 mM NaCl, 0.05% Tween 20, ph 7.4), 25° C. Purified ANG-2-His (R&D systems or in house purified) was added in various concentrations between 0.41 nM and 200 nM in solution. Association was measured by an ANG-2-injection of 3 minutes; dissociation was measured by washing the chip surface with HBS buffer for 5 minutes and a KD value was estimated using a 1:1 Langmuir binding model. Due to heterogenity of the ANG-2 preparation no 1:1 binding could be observed; KD values are thus only relative estimations. Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data. Alternatively, Ang-2 could be captured with a capture level of 2000-1700 RU via a PentaHisAntibody (PentaHis-Ab BSA-free, Qiagen No. 34660) that was immobilized on a CM5 chip via amine coupling (BSA-free) (see below).

Inhibition of huANG-2 Binding to Tie-2 (ELISA)

The interaction ELISA was performed on 384 well microtiter plates (MicroCoat, DE, Cat. No. 464718) at RT. After each incubation step plates were washed 3 times with PBST. ELISA plates were coated with 0.5 µg/ml Tie-2 protein (R&D Systems, UK, Cat. No. 313-TI) for at least 2 hours (h). Thereafter the wells were blocked with PBS supplemented with 0.2% Tween-20 and 2% BSA (Roche Diagnostics GmbH, DE) for 1 h. Dilutions of purified antibodies in PBS were incubated together with 0.2 µg/ml huAngiopoietin-2 (R&D Systems, UK, Cat. No. 623-AN) for 1 h at RT. After washing a mixture of 0.5 µg/mlbiotinylated anti-Angiopoietin-2 clone BAM0981 (R&D Systems, UK) and 1:3000 diluted streptavidin HRP (Roche Diagnostics GmbH, DE, Cat. No. 11089153001) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

Inhibition of huANG-1 Binding to Tie-2 (ELISA)

The interaction ELISA was performed on 384 well microtiter plates (MaxiSorb Nunc#442768) at RT. After each incubation step plates were washed 3 times with PBST. ELISA plates were coated with 0.5 µg/ml Tie-2 protein (R&D Systems, UK, Cat. No. 313-TI or in house produced material) for at least 2 hours (h). Thereafter the wells were blocked with PBS supplemented with 0.2% Tween-20 and 2% BSA (Roche Diagnostics GmbH, DE) for 1 h. Dilutions of purified antibodies in PBS were incubated together with 0.2 µg/ml huAngiopoietin-1 (R&D Systems #923-AN/CF or in house produced material) for 1 h at RT. After washing a mixture of 0.5 µg/ml biotinylated anti-Angiopoietin-1 clone (R&D Systems #BAF923) and 1:3000 diluted streptavidin HRP (Roche Diagnostics GmbH, DE, Cat. No. 11089153001) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

Generation of HEK293-Tie2 Cell Line

In order to determine the interference of Angiopoietin-2 antibodies with ANGPT2 stimulated Tie2 phosphorylation and binding of ANGPT2 to Tie2 on cells a recombinant HEK293-Tie cell line was generated. Briefly, a pcDNA3 based plasmid (RB22-pcDNA3 Topo hTie2) coding for full-length human Tie2 (SEQ ID 61) under control of a CMV promoter and a Neomycin resistance marker was transfected using Fugene (Roche Applied Science) as transfection reagent into HEK293 cells (ATCC) and resistant cells were selected in DMEM 10% FCS, 500 µg/ml G418. Individual clones were isolated via a cloning cylinder, and subsequently analyzed for Tie2 expression by FACS. Clone 22 was identified as clone with high and stable Tie2 expression even in the absence of G418 (HEK293-Tie2 clone22). HEK293-Tie2 clone22 was subsequently used for cellular assays: ANGPT2 induced Tie2 phosphorylation and ANGPT2 cellular ligand binding assay.

ANGPT2 Induced Tie2 Phosphorylation Assay

Inhibition of ANGPT2 induced Tie2 phosphorylation by ANGPT2 antibodies was measured according to the following assay principle. HEK293-Tie2 clone22 was stimulated with ANGPT2 for 5 minutes in the absence or presence of ANGPT2 antibody and P-Tie2 was quantified by a sandwich ELISA. Briefly, 2×105 HEK293-Tie2 clone 22 cells per well were grown over night on a Poly-D-Lysine coated 96 well-microtiter plate in 100 µl DMEM, 10% FCS, 500 µg/ml Geneticin. The next day a titration row of ANGPT2 antibodies was prepared in a microtiter plate (4-fold concentrated, 75 µl final volume/well, duplicates) and mixed with 75 µl of an ANGPT2 (R&D systems #623-AN] dilution (3.2 µg/ml as 4-fold concentrated solution). Antibodies and ANGPT2 were pre-incubated for 15 min at room temperature. 100 µl of the mix were added to the HEK293-Tie2 clone 22 cells (pre-incubated for 5 min with 1 mM NaV3O4, Sigma #S6508) and incubated for 5 min at 37° C. Subsequently, cells were washed with 200 µl ice-cold PBS+1 mM NaV3O4 per well and lysed by addition of 120 µl lysis buffer (20 mM Tris, pH 8.0, 137 mM NaCl, 1% NP-40, 10% glycerol, 2 mM EDTA, 1 mM NaV3O4, 1 mM PMSF and 10 µg/ml Aprotinin) per well on ice. Cells were lysed for 30 min at 4° C. on a microtiter plate shaker and 100 µl lysate were transferred directly into a p-Tie2 ELISA microtiter plate (R&D Systems, R&D #DY990) without previous centrifugation and without total protein determination. P-Tie2 amounts were quantified according to the manufacturer's instructions and IC50 values for inhibition were determined using XLfit4 analysis plug-in for Excel (Dose-response one site, model 205). IC50 values can be compared within on experiment but might vary from experiment to experiment.

ANGPT1 Induced Tie2 Phosphorylation Assay

Inhibition of ANGPT1 induced Tie2 phosphorylation by ANGPT1 antibodies was measured according to the following assay principle. HEK293-Tie2 clone22 was stimulated with ANGPT1 for 5 minutes in the absence or presence of ANGPT1 antibody and P-Tie2 was quantified by a sandwich ELISA. Briefly, 2×105 HEK293-Tie2 clone 22 cells per well were grown over night on a Poly-D-Lysine coated 96 well-microtiter plate in 100 µl DMEM, 10% FCS, 500 µg/ml Geneticin. The next day a titration row of ANGPT1 antibodies was prepared in a microtiter plate (4-fold concentrated, 75 µl final volume/well, duplicates) and mixed with 75 µl of an ANGPT1 (R&D systems #923-AN] dilution (0.8 µg/ml as 4-fold concentrated solution). Antibodies and ANGPT1 were pre-incubated for 15 min at room temperature. 100 µl of the mix were added to the HEK293-Tie2 clone 22 cells (pre-incubated for 5 min with 1 mM NaV3O4, Sigma #S6508) and incubated for 5 min at 37° C. Subsequently, cells were washed with 200 µl ice-cold PBS+1 mM NaV3O4 per well and lysed by addition of 120 µl lysis buffer (20 mM Tris, pH 8.0, 137 mM NaCl, 1% NP-40, 10% glycerol, 2 mM EDTA, 1 mM NaV3O4, 1 mM PMSF and 10 µg/ml Aprotinin) per well on ice. Cells were lysed for 30 min at 4° C. on a microtiter plate shaker and 100 µl lysate were transferred directly into a p-Tie2 ELISA microtiter plate (R&D Systems, R&D #DY990) without previous centrifugation and without total protein determination. P-Tie2 amounts were quantified according to the manufacturer's instructions and IC50 values for inhibition were determined using XLfit4 analysis plug-in for Excel (Dose-response one site, model 205). IC50 values can be compared within on experiment but might vary from experiment to experiment.

Example 1

Expression & Purification of Monoclonal <ANG-2> Antibodies Ang2i-LC06, Ang2i-LC07 and Ang2k-LC08

Figure 1B:
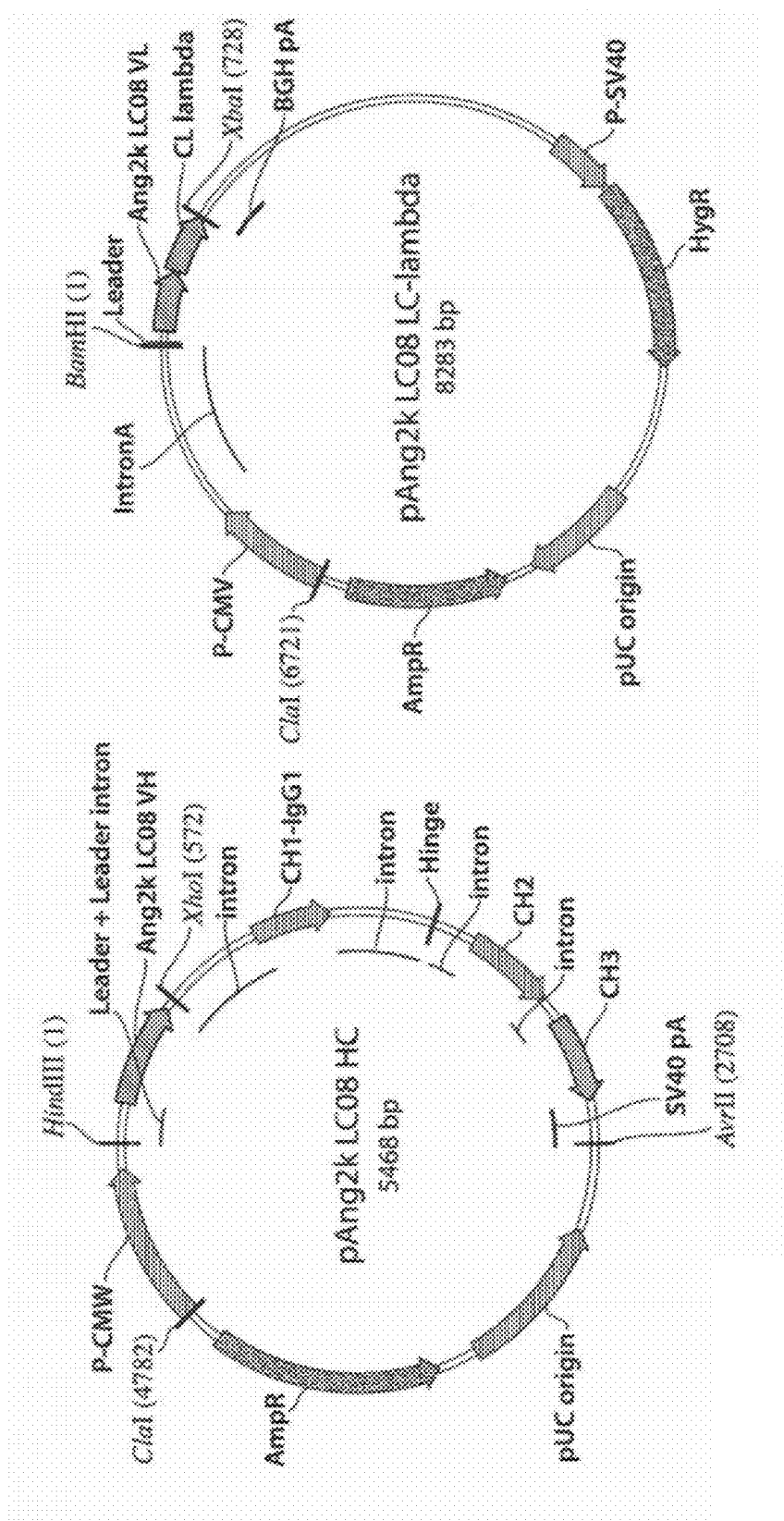

Light and heavy chains of the corresponding antibodies Ang2i-LC06, Ang2i-LC07 and Ang2k-LC08 were constructed in expression vectors as described above. The heavy chain and the kappa light was cloned in a genomic expression cassette, whereas the lambda light chain was cloned as cDNA with intron A (FIG. 1B). The plasmids were amplified in $E.$ $coli$, purified, and subsequently transfected for transient expression of recombinant proteins in HEK293-F cells (utilizing Invitrogen's FreeStyle 293 system). After 7 days, HEK 293-F cell supernatants were harvested, filtered and the antibodies were purified by protein A and size exclusion chromatography. Homogeneity of all antibodies was confirmed by SDS-PAGE under non reducing and reducing conditions and analytical size exclusion chromatography. Under reducing conditions (FIG. 1), polypeptide heavy chains of <ANG-2> antibodies showed upon SDS-PAGE apparent molecular sizes of ca. 50 kDa analogous to the calculated molecular weights, polypeptide light chains showed apparent molecular masses of 25 kDa according to their predicted size. Mass spectrometry confirmed the identity of the purified antibodies. Expression levels of all constructs were analyzed by Protein A HPLC.

Size exclusion chromatography analysis of the purified. All antibodies were prepared and analytically characterized analogously to the procedure described. The SEC data of the corresponding antibodies were summarized in the table below.

|  | Antibody chain | Theoretical mass (Da) | Experimental mass (Da) | SEC (%) main peak |
|---|---|---|---|---|
| <ANG-2>Ang-2i_LC07 | HC | 50343 | 50325 (pyro-Glu) | 99.7% |
|  | LC | 22738 | 22720 (pyro-Glu) |  |
| <ANG-2>Ang-2i_LC06 | HC | 50343 | 50325 (pyro-Glu) | 99.8% |
|  | LC | 22620 | 22605 (pyro-Glu) |  |
| <ANG-2>Ang-2k_LC08 | HC | 49544 | 49527 (pyro-Glu) | 99.8% |
|  | LC | 22685 | 22667 (pyro-Glu) |  |

Example 2

ELISA Binding Assay to Human ANG-1 and to Human ANG-2

The binding of <ANG-2> antibodies Ang2i-LC06, Ang2i-LC07 and Ang2k-LC08 to human ANG-1 and human ANG-2 was determined in an ANG-1 or ANG-2 binding ELISA as described above. Briefly, the ELISA-type assay is based on the immobilization of human wild-type Angiopoieti-1 or -2 in a microtiter plate. Binding of an antibody directed against the immobilized ANG-1 or ANG-2 is measured via an <human Fc> (anti-IgG) antibody with a POD conjugate. A dilution series of the <ANG-2> antibody allows determining an EC50 concentration. As a reference the human anti-ANG-2 antibody <ANG-2> antibody Mab536 (Oliner et al., Cancer Cell. Nov. 6 (2004) 507-16, US 2006/0122370) was used. The determined EC50 concentrations are summarized in the table below.

| Antibody | hANG-1 binding EC50 | hANG-2 binding EC50 |
|---|---|---|
| <ANG-2>MAb536 | 2538 ng/mL | 133 ng/mL |
| <ANG-2>Ang2i-LC06 | >8000 ng/mL | 84 ng/mL |
| <ANG-2>Ang2i-LC07 | >8000 ng/mL | 3006 ng/mL |
| <ANG-2>Ang2i-LC08 | 4044 ng/mL | 105 ng/mL |

All antibodies binds specifically to ANG-2. MAb536 and Ang2k-LC08 show also specific binding towards ANG-1, whereas Ang2i-LC06 and Ang2i-LC07 do not specifically bind to ANG-1 as they have an EC50-value of above 8000 ng/ml (detection limit).

Example 3

Binding to ANG-2 via Biacore

The affinity for binding to human ANGPT2 was examined with a Biacore assay as describes above. Briefly, is this assay a capturing antibody (anti-Fc) is immobilized to the surface of the Biacore chip, which captures and presents the corresponding antibody (for example Ang2i-LC06). The ligand (here ANGPT2) is captured from solution. The affinity for this interaction is determined with the assumption of a 1:1 interaction. Details of this experiment can be found in the general methods section. The affinities determined for ANGPT2-binding (KD) are summarized in the table below.

| hAng-2 | Experiment 1 | | | Experiment 2 | | | Average (from 1 + 2) | |
|---|---|---|---|---|---|---|---|---|
|  | KD (pM) | kd (1/s) | $t_{(1/2)}$diss (min) | KD (pM) | kd (1/s) | $t_{(1/2)}$diss (min) | KD (pM) | $t_{(1/2)}$diss (min) |
| Ang2i-LC06 | 11 | 7.16E−05 | 161 | 21 | 1.14E−04 | 102 | 16 | 132 |
| Ang2k-LC08 | 16 | 1.61E−04 | 72 | 27 | 2.28E−04 | 51 | 22 | 61 |
| MAb536 | 29 | 1.44E−04 | 80 | 29 | 1.25E−04 | 92 | 29 | 86 |

The antibodies Ang2i-LC06 and Ang2k bind with high affinity to ANGPT2.

Example 4

Neutralization of ANGPT1/2-Tie2 Interaction (Human)

Blocking of human ANGPT1/2/human Tie2 interaction was shown by receptor interaction ELISA. 384-well Maxisorp plates (Nunc) were coated with 0.5 μg/ml human Tie2 (R&D Systems, UK, Cat. No. 313-TI or in house produced material) for 2 h at room temperature and blocked with PBS supplemented with 0.2% Tween-20 and 2% BSA (Roche Diagnostics GmbH, DE) for 1 h at room temperature under shaking In the meantime, Dilutions of purified antibodies in PBS were incubated together with 0.2 μg/ml huAngiopoietin-1/2 (R&D Systems #923-AN/CF, R&D Systems, UK, Cat. No. 623-AN or in house produced material) for 1 h at RT. After washing a mixture of 0.5 μg/ml biotinylated anti-Angiopoietin-1/2 clone (R&D Systems #BAF923, BAM0981 R&D Systems, UK) and 1:3000 diluted streptavidin HRP (Roche Diagnostics GmbH, DE, Cat. No. 11089153001) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

The obtained inhibitory concentrations are summarized in the following table.

| Antibody | ANGPT1/Tie2 interaction ELISA | ANGPT2/Tie2 interaction ELISA |
|---|---|---|
| Ang2i-LC06 | >100 nM | 0.1 nM |
| Ang2k-LC08 | 11 nM | 0.17 nM |
| MAb536 | n.d. | 0.15 nM |

The table above shows different selectivity profiles for the two antibodies Ang2i-LC06 and Ang2k-LC08. Ang2i-LC06 is ANGPT2 selective, whereas Ang2k-LC08 is ANGPT1/2 cross reactive in inhibition for ANGPT1/2 Tie2 interaction.

Example 5

Tie2 Phosphorylation

The ability of the identified ANGPT2 antibodies to interfere with ANGPT2 and ANGPT1 mediated Tie2 phosphorylation was examined in the ANGPT2 and ANGPT1 induced Tie2 phosphorylation assays as described above. A schematic representation of the assay setup is depicted in FIG. 3.

Both antibodies Ang2i-LC06 and Ang2k-LC08 showed a dose-dependent interference with ANGPT2 stimulated Tie2 phosphorylation as shown in FIG. 4 with comparable IC50 values. Ang2i-LC06 interfered with ANGPT2 stimulated Tie2 phosphorylation with a IC50 value of approx. 508 ng/ml and Ang2k-LC08 interfered with ANGPT2 stimulated Tie2 phosphorylation with a IC50 value of approx. 499 ng/ml. In contrast, only Ang2k-LC08 interfered with ANGPT1 stimulated Tie2 phosphorylation with a IC50 value of approx. 391 ng/ml whereas Ang2i-LC06 did not interfere with ANGPT2 stimulated Tie2 phosphorylation in the same tested concentration range (FIG. 5).

Example 6

In Vivo Efficacy

Effect of Anti ANGPT Antibodies on Colo205 Xenograft Growth

In vivo efficacy of <ANGPT2> antibodies Ang2i-LC06 and Ang2k-LC08 in comparison to <ANGPT2> Mab536 in staged subcutaneous Colo205 xenograft model The purified Ang2i-LC06 and Ang2k-LC08 antibodies were compared to the antibody Mab536 in the staged subcutaneous Colo205 xenograft model (Ang2_PZ_Colo205_006) in female Scid beige mice.

Antibodies: Mab536 was provided as frozen stock solution (c=4.5 mg/mL), Ang2i-LC06 and Ang2k-LC08 were provided as frozen stock solution (c=1 mg/mL) in 20 mM Histidine, 140 mM NaCl, pH 6.0. Antibody solution was diluted appropriately in PBS from stock prior injections where required and PBS was applied as vehicle. The humanized IgG1 anti-IgE antibody Xolair (Omalizumab) served as positive control and was bought from a pharmacy.

Cell lines and culture conditions: Colo205 human colorectal cancer cells were originally obtained from ATCC and after expansion deposited in the Roche Penzberg internal cell bank. Tumor cell line was routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% CO2. Passage 3 was used for transplantation.

Animals: Female SCID beige mice (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Age of mice at start of the study was about 12-14 weeks.

Monitoring: Animals were controlled daily for clinical symptoms and detection of adverse effects. For monitoring throughout the experiment body weight of animals was documented and tumor volume was measured by caliper after staging.

Tumor cell injection: At day of injection Colo205 cells were centrifuged, washed once and resuspended in PBS. After an additional washing with PBS cell concentration and cell size were determined using a cell counter and analyzer system (Vi-CELL, Beckman Coulter). For injection of Colo205 cells, the final titer was adjusted to 5.0×10 E7 cells/ml, viability ca. 90%. Subsequently 100 μl of this suspension corresponding to 2.5*106 cells per animal was injected s.c. into the right flank of the mice.

Treatment of animals: Animal treatment started at day of randomisation, 16 days after cell transplantation (study Ang2_PZ_Colo205_006) at a mean tumor volume of 178 mm3.

Dose schedule of study Ang2_PZ_Colo205_006:

| Group | No of animals | Compound | Dose (mg/kg) | Route/Mode of administration | No of treatments | Cumulative dose (mg/kg) |
|---|---|---|---|---|---|---|
| 1 | 10 | Vehicle | | i.p. once weekly | 5 | |
| 2 | 10 | Xolair | 10 | i.p. once weekly | 5 | 50 |
| 3 | 10 | Ang2i-LC06 | 10 | i.p. once weekly | 5 | 50 |
| 5 | 10 | Ang2k-LC08 | 10 | i.p. once weekly | 5 | 50 |
| 6 | 10 | MAB536 | 10 | i.p. once weekly | 5 | 50 |

Tumor growth inhibition until Day 50 is shown in FIG. 6. The data show that the ANGPT2 selective antibody Ang2i-LC06 was the most active antibody (Tumor control ration (TCR) value 0.39). Ang2i-LC06 was more efficacious in inhibiting tumor growth than antibody MAb536 (TCR value 0.47) and the ANGPT2 selective, ANGPT1 cross-reactive antibody Ang2k-LC08 (TCR value 0.46).

Effect of Anti ANGPT Antibodies on KPL-4 Xenograft Growth

In vivo efficacy of <ANGPT2> antibodies Ang2i-LC06 and Ang2k-LC08 in comparison to <ANGPT2> Mab536 in staged orthotopic KPL-4 xenograft model. The purified Ang2i-LC06 and Ang2k-LC08 antibodies were compared to the antibody Mab536 in the staged orthotopic KPL-4 xenograft model (Ang2_PZ_KPL-4_002) in female Scid beige mice.

Antibodies: Mab536 was provided as frozen stock solution (c=4.5 mg/mL), Ang2i-LC06 and Ang2k-LC08 were provided as frozen stock solution (c=1 mg/mL) in 20 mM Histidine, 140 mM NaCl, pH 6.0. Antibody solution was diluted appropriately in PBS from stock prior injections where required and PBS was applied as vehicle.

Cell lines and culture conditions: KPL-4 human breast cancer cells were originally established from the malignant pleural effusion of a breast cancer patient with an inflammatory skin metastasis. KPL-4 cells were kindly provided by Prof J. Kurebayashi (Kawasaki Medical School, Kurashiki, Japan). Tumor cells were routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% CO2. Culture passage was performed with trypsin/EDTA 1× (PAN) splitting three times/week.

Animals: Female SCID beige mice (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Age of mice at start of the study was about 12 weeks.

Monitoring: Animals were controlled daily for clinical symptoms and detection of adverse effects. For monitoring throughout the experiment body weight of animals was documented and tumor volume was measured by caliper after staging.

Tumor cell injection: At the day of injection tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon™; 100 µm) the final cell titer was adjusted to 1.5×108/ml. Tumor cell suspension was carefully mixed with transfer pipette to avoid cell aggregation. Anesthesia was performed using a Stephens's inhalation unit for small animals with preincubation chamber (plexiglas), individual mouse nose-mask (silicon) and not flammable or explosive anesthesia compound Isoflurane (Pharmacia-Upjohn, Germany) in a closed circulation system. Two days before injection coat of the animals were shaved. For i.m.f.p. injection cells were injected orthotopically at a volume of 20 µl (3*106/animal) into the right penultimate inguinal mammary fat pad of each anesthetized mouse. For the orthotopic implantation, the cell suspension was injected through the skin under the nipple using a using a Hamilton microliter syringe and a 30 G×½" needle.

Treatment of animals started at day of randomization with tumors ranging from 60-180 mm 3.35 days after cell transplantation (study Ang2_PZ_KPL-4_002) at a mean tumor volume of ca. 90 mm3.

Dose schedule of study Ang2_PZ_KPL-4_002:

| Group | No of animals | Compound | Dose (mg/kg) | Route/Mode of administration | No of treatments | Cumulative dose (mg/kg) |
|---|---|---|---|---|---|---|
| 1 | 10 | Vehicle | | i.p. once weekly | 5 | |
| 2 | 10 | Xolair | 10 | i.p. once weekly | 5 | 50 |
| 3 | 10 | Ang2i-LC06 | 10 | i.p. once weekly | 5 | 50 |
| 5 | 10 | Ang2k-LC08 | 10 | i.p. once weekly | 5 | 50 |
| 6 | 10 | MAB536 | 10 | i.p. once weekly | 5 | 50 |

Tumor growth inhibition until day 64 is shown in FIG. 7. The data show that the ANGPT2 selective antibody Ang2i-LC06 was the most active antibody (TCR value 0.55) in the KPL-4 model. Ang2i-LC06 was more efficacious in inhibiting tumor growth than antibody MAb536 (TCR value 0.57) and the ANGPT2 selective, ANGPT1 cross-reactive antibody Ang2k-LC08 (TCR value 0.57).

Example 7

Binding to ANG-1 Via Biacore

The affinity for binding to human ANG-1 was examined with a Biacore assay: huAng-1 was immobilized on a CM5 biosensorchip using amine-coupling chemistry. The protein was injected for 20 min in sodium acetate pH 4.5 at 10 μg/ml at a flow rate of 5 μl/min. This resulted in a surface density of appr. 20000 RU. On the reference flow cell BSA was immobilized under the same conditions. The antibodies were diluted in HBS-P to 100 nM and injected for 3 min (association phase). After washing with running buffer for 3 min (dissociation phase), the surface was regenerated by injecting 10 mM sodium hydroxide for 1 min at 5 μl/min. Results are shown in FIG. 8: Ang2k_LC08 had a halftime of complex dissociation of approximately 50 s, Ang2i_LC06 of appr. 5 s and Ang2i_LC10 showed no binding to ANG-1.

Example 8

Prevention of Metastasis/Secondary Tumors In Vivo in Bearing Primary Tumors a) Prevention of Metastasis/Secondary in Mice Xenografted with Primary Colo205 Tumors Cell Lines and Culture Conditions:

Colo205 human colorectal cancer cells were originally obtained from ATCC and after expansion deposited in the Roche Penzberg internal cell bank. Tumor cell line was routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% $CO_2$. Passage 3 was used for transplantation.

Animals:

Female SCID beige mice; age 4-5 weeks at arrival (purchased from Charles River Germanyd) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Age of mice at start of the study was about 10 weeks.

Tumor Cell Injection:

At the day of injection, Colo205 tumor cells were harvested (trypsin-EDTA) from culture flasks (Greiner) and transferred into 50 ml culture medium, washed once and resuspended in PBS. After an additional washing step with PBS and filtration (cell strainer; Falcon ø 100 μm) the final cell titer was adjusted to $2.5 \times 10^7$/ml. Tumor cell suspension was carefully mixed with transfer pipette to avoid cell aggregation. After this, cell suspension was filled into a 1.0 ml tuberculin syringe (Braun Melsungen) using a wide needle (1.10×40 mm); for injection needle size was changed (0.45× 25 mm) and for every injection a new needle was used. Anesthesia was performed using a Stephens inhalation unit for small animals with preincubation chamber (plexiglas), individual mouse nose-mask (silicon) and not flammable or explosive anesthesia compound Isoflurane (cp-pharma) in a closed circulation system. Two days before injection coat of the animals were shaved and for cell injection skin of anaesthetized animals was carefully lifted up with an anatomic forceps and 100 μl cell suspension (=$2.5 \times 10^6$ cells) was injected subcutaneously in the right flank of the animals. Tumor growth of the primary tumors was monitored (data not shown)

Monitoring of Secondary Tumors e.g. in the Lung by Quantification of Human Alu Sequences At study termination (day 103) lungs were collected from animals of all groups. Briefly, samples are transferred immediately into fluid nitrogen. In a further step total DNA was isolated from the samples with MagNA Pure LC Instrument according to manufacturer's instructions. Human Alu specific primers were chosen for selective amplification of Alu sequences by quantitative PCR (LightCycler instrument). (T. Schneider et. al., Clin. Exp. Metas. 2002; 19: 571-582).

Treatment of Animals

Treatment of animals with Avastin (10 mg/kg i.p. once weekly) was started 14 days after cell transplantation (study Ang2_PZ_Colo205_008) at a mean tumor volume of 340 $mm^3$. After 7 weeks mice were randomized for subsequent secondary treatment starting at day 51 with compounds listed in table below. Secondary treatment starting at day 51 of Study Ang2_PZ_Colo205_008.

| Group | No of animals | Compound | Dose (mg/kg) | Route/Mode of administration | No of treatments | Cumulative dose (mg/kg) |
|---|---|---|---|---|---|---|
| | 10 | Avastin | 10 mg/kg | i.p. once weekly | 11 | 110 |
| | 10 | LC06 + Avastin | 10 mg/kg 10 mg/kg | i.p. once weekly i.p. once weekly | 6 11 | 60 110 |
| | 10 | LC06 | 10 mg/kg | i.p. once weekly | 6 | 60 |

Results of Prevention of Metastasis/Secondary Tumors (in the Lung) are Listed in the Table Below and Shown in FIG. 9A

TABLE 1

Quantification of human ALU DNA in the lungs of mice originally bearing primary Colo205 tumors, after treatment with different antibodies

| Avastin | | Avastin + Ang2i-LC06 | | Ang2i_LC06 | |
|---|---|---|---|---|---|
| 101 | 0.0264 | 201 | 0.0042 | 301 | 0.0047 |
| 102 | 5.6740 | 202 | 0.0044 | 302 | 0.0055 |
| 103 | 0.0307 | 203 | 0.0065 | 303 | 0.0050 |
| 104 | 0.0203 | 204 | 0.0081 | 304 | 0.0064 |
| 105 | 0.0215 | 205 | 0.0063 | 305 | 0.0062 |
| 106 | 0.0338 | 206 | 0.0061 | 306 | 0.0066 |
| 107 | 0.0075 | 207 | 0.0053 | 307 | 0.0250 |
| 108 | 0.0113 | 208 | 0.0506 | 308 | 0.0062 |
| 109 | 0.0087 | 209 | 0.0065 | 309 | 0.0067 |

TABLE 1-continued

Quantification of human ALU DNA in the lungs of
mice originally bearing primary Colo205 tumors,
after treatment with different antibodies

| Avastin | | Avastin + Ang2i-LC06 | | Ang2i_LC06 | |
|---|---|---|---|---|---|
| 110 | 0.0587 | 210 | 0.0160 | 310 | 0.0064 |
| mean | 0.5893 | | 0.0114 | | 0.0079 |
| median | 0.0240 | | 0.0064 | | 0.0063 |

Results show a clearly improved prevention of secondary tumors/metastasis by ANG2i-LC06 compared with Avastin
b) Prevention of Metastasis/Secondary in Mice Xenografted with Primary KPL-4 Tumors Tumor Cell Line The human breast cancer cell line KPL-4 (kindly provided by Prof. J. Kurebayashi) has been established from the malignant pleural effusion of a breast cancer patient with an inflammatory skin metastasis. Tumor cells are routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% $CO_2$. Culture passage is performed with trypsin/EDTA 1× (PAN) splitting three times/week.

Mice

After arrival, female SCID beige mice (age 10-12 weeks; body weight 18-20 g) Charles River, Sulzfeld, Germany) were maintained in the quarantine part of the animal facility for one week to get them accustomed to the new environment and for observation. Continuous health monitoring was carried out. The mice were kept under SPF-conditions according to the international guidelines (GV-Solas; Felasa; TierschG) with daily cycles of 12 h light/12 h darkness. Diet food (Kliba Provimi 3347) and water (filtered) were provided ad libitum. Experimental study protocol was reviewed and approved by the local government (Regierung von Oberbayern; registration no. 211.2531.2-22/2003).

Tumor Cell Injection

At the day of injection tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon Ø100 μm) the final cell titer was adjusted to $1.5×10^8$/ml. Tumor cell suspension was carefully mixed with transfer pipette to avoid cell aggregation. Anesthesia is performed using a Stephens inhalation unit for small animals with preincubation chamber (plexiglas), individual mouse nose-mask (silicon) and not flammable or explosive anesthesia compound Isoflurane (Pharmacia-Upjohn, Germany) in a closed circulation system. Two days before injection coat of the animals were shaved. For i.m.f.p. injection cells were injected orthotopically at a volume of 20 μl into the right penultimate inguinal mammary fat pad of each anesthetized mouse. For the orthotopic implantation, the cell suspension was injected through the skin under the nipple using a using a Hamilton microliter syringe and a 30 G×½" needle. Tumor growth of the primary tumors was monitored (data not shown)

Monitoring of Secondary Tumors e.g. in the Lung by Quantification of Human Alu Sequences At study termination (day 103) lungs were collected from animals of all groups. Briefly, samples are transferred immediately into fluid nitrogen. In a further step total DNA was isolated from the samples with MagNA Pure LC Instrument according to manufacturer's instructions. Human Alu specific primers were chosen for selective amplification of Alu sequences by quantitative PCR (LightCycler instrument). (T. Schneider et. al., Clin. Exp. Metas. 2002; 19: 571-582)

Treatment of Animals

Treatment of animals was started 35 days after cell transplantation at a mean tumor volume of 60-160 $mm^3$. Compounds and dose schedule is listed in the table below.

| Group | No of animals | Compound | Dose (mg/kg) | Route/Mode of administration | No of treatments | Cumulative dose (mg/kg) |
|---|---|---|---|---|---|---|
| | 10 | Vehicle | | i.p. twice weekly | 5 | |
| | 10 | Xolair | 10 | i.p. twice weekly | 5 | 50 |
| | 10 | Ang2i_LC06 | 10 | i.p. once weekly | 4 | 40 |
| | 10 | Ang2i_LC07 | 10 | i.p. once weekly | 4 | 40 |
| | 10 | Ang2k_LC08 | 10 | i.p. once weekly | 4 | 40 |

Results of prevention of metastasis/secondary tumors (in the lung) are listed in the table below and shown in FIG. 9B

TABLE 2

Quantification of human ALU DNA in the lungs of mice originally bearing
primary KPL4 tumors, after treatment with different antibodies

| Vehicle | | Xolair | | Ang2i_LC06 | | Ang2i_LC07 | | Ang2i_LC08 | |
|---|---|---|---|---|---|---|---|---|---|
| 101 | 0.0098 | 201 | 0.0157 | | | 401 | 0.0273 | 501 | 0.0069 |
| 102 | 0.0090 | 202 | 0.0516 | 302 | 0.0076 | 402 | 0.0060 | 502 | 0.0261 |
| 103 | 0.0119 | 203 | 0.0108 | 303 | 0.0413 | 403 | 0.0046 | 503 | 0.0067 |
| 104 | 0.0405 | 204 | 0.0148 | 304 | 0.0042 | 404 | 0.0164 | 504 | 0.0044 |
| | | 205 | 0.0020 | 305 | 0.0041 | 405 | 0.0040 | 505 | 0.0039 |
| 106 | 0.0381 | 206 | 0.0340 | 306 | 0.0093 | 406 | 0.0044 | 506 | 0.0051 |
| 107 | 0.0281 | 207 | 0.0141 | 307 | 0.0038 | 407 | 0.0060 | 507 | 0.0037 |
| | | 208 | 0.0422 | 308 | 0.0044 | 408 | 0.0174 | 508 | 0.0037 |
| 109 | 0.0121 | 209 | 0.0227 | 309 | 0.0036 | 409 | 0.0314 | 509 | 0.0051 |
| 110 | 0.0143 | 210 | 0.0383 | 310 | 0.0094 | 410 | 0.0083 | 540 | 0.0200 |
| median | 0.0132 | | 0.0192 | | 0.0044 | | 0.0072 | | 0.0051 |
| mean | 0.0205 | | 0.0246 | | 0.0098 | | 0.0126 | | 0.0086 |

Results show a very efficient prevention of secondary tumors/metastasis by ANG2i-LC06, ANG2i-LC07, ANG2k-LC08.

Example 9

Effects in the Treatment of Retinopathy

Methods

C57/Bl6 pups are cross fostered to CD1 nursing dams and are exposed to 75% oxygen from P7 to P12 (PRO-OX 110 chamber oxygen controller, Biospherix Ltd, Redfield, N.Y.) which induces vessel obliteration and cessation of capillaries in the centre of the retina. The pups and nursing dams are placed in normal air leading to relative hypoxia and the induction of neovascularisation. On P13, pups were anaesthetised using isofluorane (5% induction, 3% maintenance combined with 1.5% oxygen) and the eye was exposed and 1 µl intraocular injections using a Nanofil syringe fitted with a 35 gauge needle (WPI, Sarasota, Fla.) into the left eye was performed. On P17, both eyes were dissected, fixed in 4% paraformaldehyde for 4 h at 4° C. and retinas were dissected. Retinas were permeabilised in PBS containing 0.5% Triton X-100 and 1% bovine serum albumin, stained with 20 µg/ml biotinylated isolectin B4 (Sigma Aldrich, Gillingham, UK) in PBS pH 6.8, 1% Triton-X100, 0.1 mM $CaCl_2$, 0.1 mM $MgCl_2$, followed by 20 µg/ml ALEXA 488-streptavidin (Molecular Probes, Eugene, Oreg.) and flat mounted in Vectashield (Vector Laboratories, Burlingame, Calif.). Retinas were imaged using a Nikon epi-fluorescence microscope at 4× magnification. Quantification of neovascular and ischaemic areas were performed in a blinded fashion using Photoshop CS3 along with Image J (NIH) and expressed as percentage of total retinal area (=normal+ischaemic+neovascular).

Results

Figure 10B:
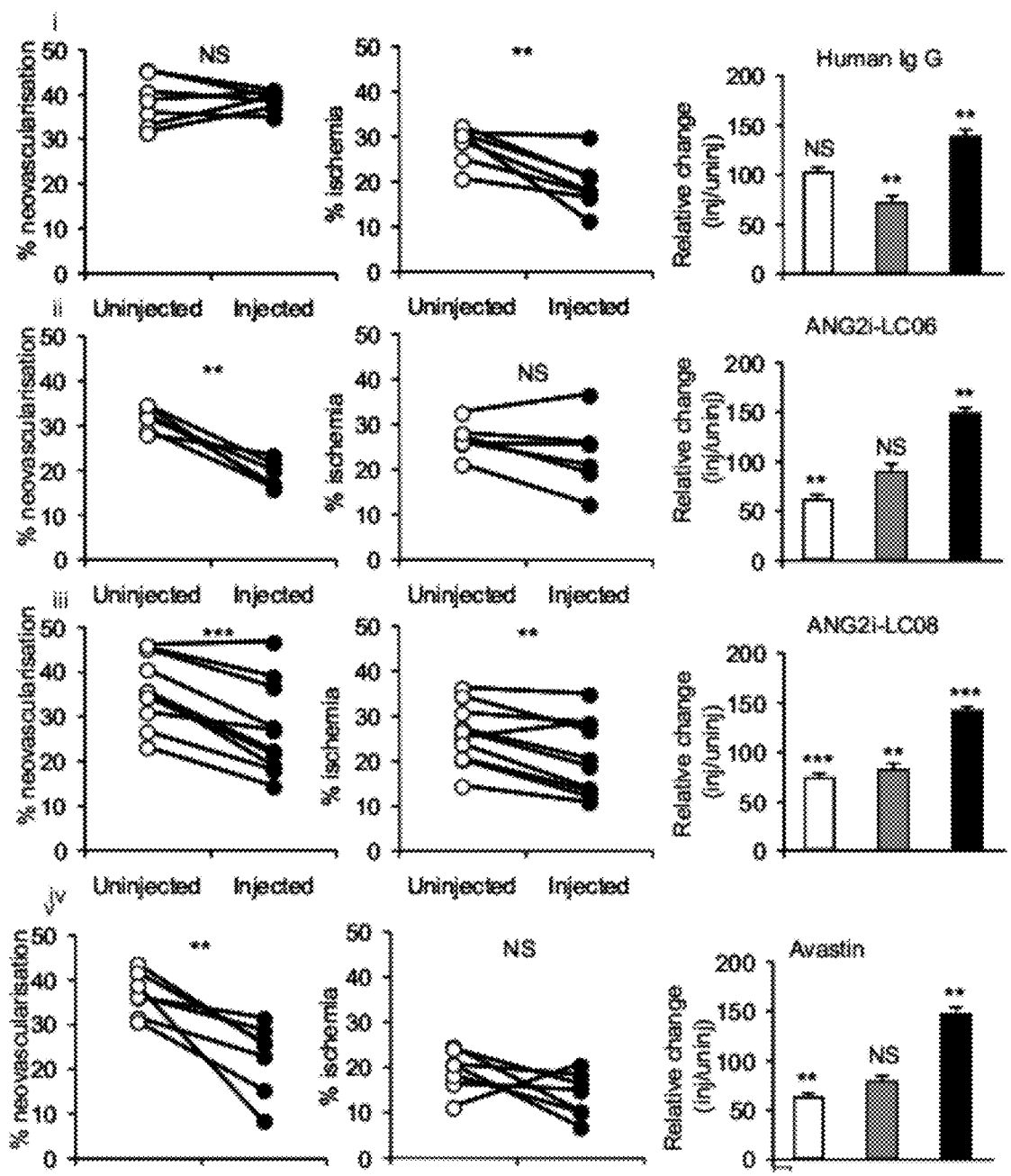

FIG. 10A show representative flat mounted retinas with the retinal vasculature visualised by isolectin staining. The centre ischemic areas induce neovascularisation and re-growth of the retinal vessels by upregulation of angiogenic inducers. The neovascular front is hyperproliferative leading to tortuous vessels in an irregular vessel pattern. The most outer areas contain the normal unaffected vessels. Quantification of retinal flat mounts showed that inhibition of VEGF with Avastin reduced retinal neovascularisation (see FIG. 10B, uninjected 36.7±1.8% to injected 22.4±3.0%) as expected. Inhibition of Ang2 using antibodies LC06 or LC08 also led to a reduction in neovascularisation (31.5±1.1% to 18.8±1.3% and 34.0±3.1% to 25.4±3.4%). Control injection of human Ig G had no effect on neovascularisation (see FIG. 10B, 38.3±1.1% to 38.3±0.8%).

The invention claimed is:

1. A prokaryotic or eukaryotic host cell comprising: (A) an expression vector comprising a nucleic acid encoding a heavy chain of an antibody which binds specifically to human angiopoietin-2 (ANG-2), wherein the variable domain of said heavy chain comprises a CDR3 region having the sequence of SEQ ID NO: 1, a CDR2 region having the sequence of SEQ ID NO: 2, and a CDR1 region having the sequence of SEQ ID NO: 3; and (B) an expression vector comprising a nucleic acid encoding a light chain of said antibody, wherein the variable domain of said light chain comprises a CDR3 region having the sequence of SEQ ID NO: 4, a CDR2 region having the sequence of SEQ ID NO: 5, and a CDR1 region having the sequence of SEQ ID NO: 6.

2. A host cell according to claim 1 wherein said variable domain of said heavy chain has the sequence of SEQ ID NO: 7.

3. A host cell according to claim 1 wherein said variable domain of said light chain has the sequence of SEQ ID NO: 8.

4. A host cell according to claim 1 wherein said variable domain of said heavy chain has the sequence of SEQ ID NO: 7 and said variable domain of said light chain has the sequence of SEQ ID NO: 8.

* * * * *